United States Patent
Agarwal et al.

(12) 
(10) Patent No.: US 6,518,488 B1
(45) Date of Patent: Feb. 11, 2003

(54) NUCLEIC ACID MOLECULES AND OTHER MOLECULES ASSOCIATED WITH THE β-OXIDATION PATHWAY

(75) Inventors: Ameeta Agarwal, Chesterfield, MO (US); Jingdong Liu, Ballwin, MO (US); Devlina Lahiri, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/621,816

(22) Filed: Jul. 21, 2000

(51) Int. Cl.$^7$ .............................. A01H 5/00; C12N 5/04; C12N 15/82; C07H 21/02
(52) U.S. Cl. ........................ 800/298; 800/281; 800/312; 800/314; 800/320.1; 800/320.3; 435/419; 536/23.2; 536/23.6
(58) Field of Search ................................ 536/23.1, 23.2, 536/23.6; 800/281, 298, 314, 320.3, 320.1, 312; 435/69.1, 468, 419

(56) References Cited

U.S. PATENT DOCUMENTS 5,824,877 A * 10/1998 Hinchee et al. ............. 800/205

OTHER PUBLICATIONS

Adams et al., *Science*, 252:1651–1656 (1991).
Ebert et al., *Proc. Natl. Acad. Sci. USA*, 84:5745–5749 (1987).
Efstratiadis et al., *Cell* 7:279–288 (1976).
Ko, *Nucleic Acids Research*, 18:5705–5711 (1990).
Kurata et al., *Nature Genetics*, 8:362–372 (1994).
McCombie et al., *Nature Genetics*, 1:124–131 (1992).
Okubo et al., *Nature Genetics*, 2:173–179 (1992).
Yomo et al., *Planta*, 112:35–43 (1973).
Venter, J. Craig, et al., The Sequence of the Human Genome, *Science*, 291: 1304–1351 (2001).
Woese, Carl R., et al., Conservation of Primary Structure in 16S rRNA, *Nature*, 254: 83–86 (1975).
Bork et al, "Go hunting in sequence databases but watch our for the traps", Oct. 1996, TIG vol. 12 No. 10, pp. 425–427.*
Brenner, "Errors in genome annotation", Apr. 1999, TIG, vol. 15 No. 4, pp. 132–133.*
Smith et al, The Challenges of genome sequence annotation or "The deveil is in the details", Nov. 1997, Nature Biotechnology pp. vol. 15, 1222–1223.*
Doerks et al, Protein annotation: detective work for function prediction, Jun. 1998, TIG vol. 14 No. 6, pp. 248–250.*

* cited by examiner

*Primary Examiner*—Elizabeth F. McElwain
(74) *Attorney, Agent, or Firm*—Lawrence M. Lavin, Jr.; Arnold & Porter

(57) ABSTRACT

The present invention is in the field of plant biochemistry, particularly as it pertains to the β-oxidation pathway. More specifically, the invention relates to nucleic acid molecules that encode proteins and fragments of proteins associated with the b-oxidation pathway, the proteins and fragments of proteins so encoded, and antibodies capable of binding the proteins. The invention also relates to methods of using the nucleic acid molecules, proteins, and fragments of proteins.

4 Claims, No Drawings ent of plant development.

SEQUENCE LISTING

<160> NUMBER OF SEQ ID NOS: 10

<210> SEQ ID NO 1
<211> LENGTH: 2491
<212> TYPE: DNA
<213> ORGANISM: Zea mays
<220> FEATURE:

-continued

```
<221> NAME/KEY: CDS
<222> LOCATION: (1)..(2103)

<400> SEQUENCE: 1 att cgg ctc gag agt tgg agc agg tct ggg tct ggc cgc gtg agt tat    48
Ile Arg Leu Glu Ser Trp Ser Arg Ser Gly Ser Gly Arg Val Ser Tyr
 1               5                  10                  15 ttc cca gcc agg cat ctg aga gct ttg gtc ttg acc tcg aca gag atc    96
Phe Pro Ala Arg His Leu Arg Ala Leu Val Leu Thr Ser Thr Glu Ile
             20                  25                  30 gcc atg gac gca tcg gcg gag gtg gac cac ctc gcc gcc gag agg tcg   144
Ala Met Asp Ala Ser Ala Glu Val Asp His Leu Ala Ala Glu Arg Ser
         35                  40                  45 gcc gcg cgc ttc gac gtc gag gcg atg aag gtt gca tgg gct ggc tcg   192
Ala Ala Arg Phe Asp Val Glu Ala Met Lys Val Ala Trp Ala Gly Ser
     50                  55                  60 cga cac gcc gtc gaa gtc ggc gac cgc atg gcc cga ctc gtc gcg tcc   240
Arg His Ala Val Glu Val Gly Asp Arg Met Ala Arg Leu Val Ala Ser
 65                  70                  75                  80 gac cct gtc ttc cgc aag gat aac agg acc atg ctc tcc agg aag gac   288
Asp Pro Val Phe Arg Lys Asp Asn Arg Thr Met Leu Ser Arg Lys Asp
                 85                  90                  95 ttg ttt aag gac act cta aga aag gca gcc cat gca tgg aag cgt att   336
Leu Phe Lys Asp Thr Leu Arg Lys Ala Ala His Ala Trp Lys Arg Ile
            100                 105                 110 gtc gaa cta cgt ctc aca gag gag gaa gca ggt atg ctg agg cta tat   384
Val Glu Leu Arg Leu Thr Glu Glu Glu Ala Gly Met Leu Arg Leu Tyr
        115                 120                 125 gtc gat cag cct ggt tat gtt gat ctg cat tgg ggc atg ttt gtt cct   432
Val Asp Gln Pro Gly Tyr Val Asp Leu His Trp Gly Met Phe Val Pro
    130                 135                 140 gct ata aaa ggt caa ggt act gag gag cag cag aaa aag tgg tta cca   480
Ala Ile Lys Gly Gln Gly Thr Glu Glu Gln Gln Lys Lys Trp Leu Pro
145                 150                 155                 160 atg gct tac aag ttc caa ata att ggg tgc tat gct cag act gaa ctc   528
Met Ala Tyr Lys Phe Gln Ile Ile Gly Cys Tyr Ala Gln Thr Glu Leu
                165                 170                 175 ggt cat ggc tca aac gtt cag ggc ctt gaa aca act gcc aca ttt gat   576
Gly His Gly Ser Asn Val Gln Gly Leu Glu Thr Thr Ala Thr Phe Asp
            180                 185                 190 cca aag act gat gag ttt gtc atc cac agt cca act ctg acc tcc agc   624
Pro Lys Thr Asp Glu Phe Val Ile His Ser Pro Thr Leu Thr Ser Ser
        195                 200                 205 aaa tgg tgg cct ggt ggc ttg ggg aaa gct tcc act cat gca gtg gtg   672
Lys Trp Trp Pro Gly Gly Leu Gly Lys Ala Ser Thr His Ala Val Val
    210                 215                 220 tat gct cgg ctg ata act gaa gga aag gac tat ggt ata cat ggt ttc   720
Tyr Ala Arg Leu Ile Thr Glu Gly Lys Asp Tyr Gly Ile His Gly Phe
225                 230                 235                 240 att gtg caa ctg cga agc tta gag gat cac tcc cct ctt cct ggt gtt   768
Ile Val Gln Leu Arg Ser Leu Glu Asp His Ser Pro Leu Pro Gly Val
                245                 250                 255 act ctg ggt gat att ggt gga aaa ttt ggc agt ggt gca tat aac agt   816
Thr Leu Gly Asp Ile Gly Gly Lys Phe Gly Ser Gly Ala Tyr Asn Ser
            260                 265                 270 atg gac aat ggt gtt ctg cga ttt gac cat gtg cgc ata cca agg gat   864
Met Asp Asn Gly Val Leu Arg Phe Asp His Val Arg Ile Pro Arg Asp
        275                 280                 285 caa atg ttg atg agg ctt tca caa gtt aca agg gag ggg aaa tat gtt   912
Gln Met Leu Met Arg Leu Ser Gln Val Thr Arg Glu Gly Lys Tyr Val
```

```
            290                 295                 300
cat tca gat gtc cca aag cag ctg ctt tat ggg aca atg gtt ttt gtt    960
His Ser Asp Val Pro Lys Gln Leu Leu Tyr Gly Thr Met Val Phe Val
305                 310                 315                 320 cgc cag aca ata gtc gca gat gct tct aag gct ttg tcc cgt gct gtt   1008
Arg Gln Thr Ile Val Ala Asp Ala Ser Lys Ala Leu Ser Arg Ala Val
                325                 330                 335 tgc att gct gta cga tac agc gcc atc cga aag cag ttt ggc tct caa   1056
Cys Ile Ala Val Arg Tyr Ser Ala Ile Arg Lys Gln Phe Gly Ser Gln
                340                 345                 350 gat ggt gga cct gag act aag gtc ctt gat tac aag act caa caa agc   1104
Asp Gly Gly Pro Glu Thr Lys Val Leu Asp Tyr Lys Thr Gln Gln Ser
            355                 360                 365 aga ctc ttt ccg ttg ctg gct tca gca tat gca ttt aga ttt gtg ggt   1152
Arg Leu Phe Pro Leu Leu Ala Ser Ala Tyr Ala Phe Arg Phe Val Gly
        370                 375                 380 gac tgg ctg aag tgg cta tac atg gat gtc act cag aaa ctg gaa gct   1200
Asp Trp Leu Lys Trp Leu Tyr Met Asp Val Thr Gln Lys Leu Glu Ala
385                 390                 395                 400 aaa gac tac tca aca ctg caa gaa gcc cat gcc tgt act gct ggt ttg   1248
Lys Asp Tyr Ser Thr Leu Gln Glu Ala His Ala Cys Thr Ala Gly Leu
                405                 410                 415 aag gct gtg aca aca tct gca aca gct gat gcc att gaa gaa tgt aga   1296
Lys Ala Val Thr Thr Ser Ala Thr Ala Asp Ala Ile Glu Glu Cys Arg
                420                 425                 430 aag ctc tgt ggc gga cat ggt tac ctg aac agc agt ggg ctt cct gaa   1344
Lys Leu Cys Gly Gly His Gly Tyr Leu Asn Ser Ser Gly Leu Pro Glu
            435                 440                 445 ttg ttt gct gtc tat gtt cct gct tgc act tat gaa gga gac aat att   1392
Leu Phe Ala Val Tyr Val Pro Ala Cys Thr Tyr Glu Gly Asp Asn Ile
        450                 455                 460 gtt ctg ctt ttg cag gtt gca agg att cta atg aag acc gta tct caa   1440
Val Leu Leu Leu Gln Val Ala Arg Ile Leu Met Lys Thr Val Ser Gln
465                 470                 475                 480 ttg aca tct gga aag caa cct gtt ggt aca atg gct tac atg ggc aat   1488
Leu Thr Ser Gly Lys Gln Pro Val Gly Thr Met Ala Tyr Met Gly Asn
                485                 490                 495 gta caa tat ctg atg caa tgc aaa tgt gct gtt aac aca gcc gaa gat   1536
Val Gln Tyr Leu Met Gln Cys Lys Cys Ala Val Asn Thr Ala Glu Asp
                500                 505                 510 tgg ctt aac cct gtt gcc ata caa gag gcg ttt gaa gcc cgg gct ctc   1584
Trp Leu Asn Pro Val Ala Ile Gln Glu Ala Phe Glu Ala Arg Ala Leu
            515                 520                 525 agg atg gca gta aac tgt gcc cag aac ata ggc caa gca gca aac caa   1632
Arg Met Ala Val Asn Cys Ala Gln Asn Ile Gly Gln Ala Ala Asn Gln
        530                 535                 540 gaa gaa ggt ttc tat gag cgg tcc cct gat ttg cta gag gct gca gta   1680
Glu Glu Gly Phe Tyr Glu Arg Ser Pro Asp Leu Leu Glu Ala Ala Val
545                 550                 555                 560 gct cac atc cag ttg gtc att gta acc aag ttc att gcg aag gta cag   1728
Ala His Ile Gln Leu Val Ile Val Thr Lys Phe Ile Ala Lys Val Gln
                565                 570                 575 cag gac att cct gga cct gga gtg aag gaa cag ctc cag aac ctt tgc   1776
Gln Asp Ile Pro Gly Pro Gly Val Lys Glu Gln Leu Gln Asn Leu Cys
                580                 585                 590 aat gtc tat gcc ctc tac att ctc cac aag cac ctg ggc gac ttc ctg   1824
Asn Val Tyr Ala Leu Tyr Ile Leu His Lys His Leu Gly Asp Phe Leu
            595                 600                 605 gca acc ggg tgc atc aca ccc aag cag gga gcg ctg gca aac gag cag   1872
```

-continued

```
                                                                        1920
Ala Thr Gly Cys Ile Thr Pro Lys Gln Gly Ala Leu Ala Asn Glu Gln
        610                 615                 620
ctg ggc aag ctt tac gca cag gtg cgt cca aat gct gtt gcg ctg gtg         1920
Leu Gly Lys Leu Tyr Ala Gln Val Arg Pro Asn Ala Val Ala Leu Val
625                 630                 635                 640
gat gcc ttc aac tac aca gac cac tac ctg ggg tct gtg ctg ggg cgg         1968
Asp Ala Phe Asn Tyr Thr Asp His Tyr Leu Gly Ser Val Leu Gly Arg
                645                 650                 655
tac gat ggg aat gtg tac cca gcg ctg tac gag gag gcg tgg aag gac         2016
Tyr Asp Gly Asn Val Tyr Pro Ala Leu Tyr Glu Glu Ala Trp Lys Asp
            660                 665                 670
cct ctg aac gag acg gtg gtg ccc gag ggg tac cac gag tac ctc cgc         2064
Pro Leu Asn Glu Thr Val Val Pro Glu Gly Tyr His Glu Tyr Leu Arg
        675                 680                 685
ccc ttg ctc aag cag cag ctc aag ctc tcc agg ctc tag tctgatcggc          2113
Pro Leu Leu Lys Gln Gln Leu Lys Leu Ser Arg Leu
690                 695                 700 tacccccct ggaattctcc atggcggctg ccttctcaga gaatctcacg cgacctccga        2173
atgaaagtga tgtaagctac taacgattct tgttagagcc aggaaagagg ctctccagcc      2233
aattataaat ttattcctca agctctgagg atcaagttca agctgtggat tatataggaa      2293
gcacgtttaa taattaataa agagggagag gatgagcatc tctctgttgc tgctcaagtg      2353
ttgtgcgcag tgcgagtagt agaatgaata tatacgagtg cgtgtattgt atggtgaatt      2413
gaagttccat tgtttgcta aaagtatatc agaaacaat ggcttgattt gcctaagtcc        2473
aaaaaaaaaa aaaaaagg                                                    2491
```

<210> SEQ ID NO 2
<211> LENGTH: 700
<212> TYPE: PRT
<213> ORGANISM: Zea mays

<400> SEQUENCE: 2

```
Ile Arg Leu Glu Ser Trp Ser Arg Ser Gly Ser Gly Arg Val Ser Tyr
1               5                   10                  15
Phe Pro Ala Arg His Leu Arg Ala Leu Val Leu Thr Ser Thr Glu Ile
                20                  25                  30
Ala Met Asp Ala Ser Ala Glu Val Asp His Leu Ala Ala Glu Arg Ser
            35                  40                  45
Ala Ala Arg Phe Asp Val Glu Ala Met Lys Val Ala Trp Ala Gly Ser
        50                  55                  60
Arg His Ala Val Glu Val Gly Asp Arg Met Ala Arg Leu Val Ala Ser
65                  70                  75                  80
Asp Pro Val Phe Arg Lys Asp Asn Arg Thr Met Leu Ser Arg Lys Asp
                85                  90                  95
Leu Phe Lys Asp Thr Leu Arg Lys Ala Ala His Ala Trp Lys Arg Ile
                100                 105                 110
Val Glu Leu Arg Leu Thr Glu Glu Ala Gly Met Leu Arg Leu Tyr
                115                 120                 125
Val Asp Gln Pro Gly Tyr Val Asp Leu His Trp Gly Met Phe Val Pro
            130                 135                 140
Ala Ile Lys Gly Gln Gly Thr Glu Glu Gln Lys Lys Trp Leu Pro
145                 150                 155                 160
Met Ala Tyr Lys Phe Gln Ile Ile Gly Cys Tyr Ala Gln Thr Glu Leu
                165                 170                 175
Gly His Gly Ser Asn Val Gln Gly Leu Glu Thr Thr Ala Thr Phe Asp
```

-continued

```
                    180                 185                 190
Pro Lys Thr Asp Glu Phe Val Ile His Ser Pro Thr Leu Thr Ser Ser
                195                 200                 205
Lys Trp Trp Pro Gly Gly Leu Gly Lys Ala Ser Thr His Ala Val Val
            210                 215                 220
Tyr Ala Arg Leu Ile Thr Glu Gly Lys Asp Tyr Gly Ile His Gly Phe
225                 230                 235                 240
Ile Val Gln Leu Arg Ser Leu Glu Asp His Ser Pro Leu Pro Gly Val
                245                 250                 255
Thr Leu Gly Asp Ile Gly Gly Lys Phe Gly Ser Gly Ala Tyr Asn Ser
            260                 265                 270
Met Asp Asn Gly Val Leu Arg Phe Asp His Val Arg Ile Pro Arg Asp
        275                 280                 285
Gln Met Leu Met Arg Leu Ser Gln Val Thr Arg Glu Gly Lys Tyr Val
    290                 295                 300
His Ser Asp Val Pro Lys Gln Leu Leu Tyr Gly Thr Met Val Phe Val
305                 310                 315                 320
Arg Gln Thr Ile Val Ala Asp Ala Ser Lys Ala Leu Ser Arg Ala Val
                325                 330                 335
Cys Ile Ala Val Arg Tyr Ser Ala Ile Arg Lys Gln Phe Gly Ser Gln
            340                 345                 350
Asp Gly Gly Pro Glu Thr Lys Val Leu Asp Tyr Lys Thr Gln Gln Ser
        355                 360                 365
Arg Leu Phe Pro Leu Leu Ala Ser Ala Tyr Ala Phe Arg Phe Val Gly
    370                 375                 380
Asp Trp Leu Lys Trp Leu Tyr Met Asp Val Thr Gln Lys Leu Glu Ala
385                 390                 395                 400
Lys Asp Tyr Ser Thr Leu Gln Glu Ala His Ala Cys Thr Ala Gly Leu
                405                 410                 415
Lys Ala Val Thr Thr Ser Ala Thr Ala Asp Ala Ile Glu Glu Cys Arg
            420                 425                 430
Lys Leu Cys Gly Gly His Gly Tyr Leu Asn Ser Ser Gly Leu Pro Glu
        435                 440                 445
Leu Phe Ala Val Tyr Val Pro Ala Cys Thr Tyr Glu Gly Asp Asn Ile
    450                 455                 460
Val Leu Leu Leu Gln Val Ala Arg Ile Leu Met Lys Thr Val Ser Gln
465                 470                 475                 480
Leu Thr Ser Gly Lys Gln Pro Val Gly Thr Met Ala Tyr Met Gly Asn
                485                 490                 495
Val Gln Tyr Leu Met Gln Cys Lys Cys Ala Val Asn Thr Ala Glu Asp
            500                 505                 510
Trp Leu Asn Pro Val Ala Ile Gln Glu Ala Phe Glu Ala Arg Ala Leu
        515                 520                 525
Arg Met Ala Val Asn Cys Ala Gln Asn Ile Gly Gln Ala Ala Asn Gln
    530                 535                 540
Glu Glu Gly Phe Tyr Glu Arg Ser Pro Asp Leu Leu Glu Ala Ala Val
545                 550                 555                 560
Ala His Ile Gln Leu Val Ile Val Thr Lys Phe Ile Ala Lys Val Gln
                565                 570                 575
Gln Asp Ile Pro Gly Pro Gly Val Lys Glu Gln Leu Gln Asn Leu Cys
            580                 585                 590
Asn Val Tyr Ala Leu Tyr Ile Leu His Lys His Leu Gly Asp Phe Leu
        595                 600                 605
```

```
Ala Thr Gly Cys Ile Thr Pro Lys Gln Gly Ala Leu Ala Asn Glu Gln
    610                 615                 620

Leu Gly Lys Leu Tyr Ala Gln Val Arg Pro Asn Ala Val Ala Leu Val
625                 630                 635                 640

Asp Ala Phe Asn Tyr Thr Asp His Tyr Leu Gly Ser Val Leu Gly Arg
                645                 650                 655

Tyr Asp Gly Asn Val Tyr Pro Ala Leu Tyr Glu Ala Trp Lys Asp
                660                 665                 670

Pro Leu Asn Glu Thr Val Val Pro Glu Gly Tyr His Glu Tyr Leu Arg
            675                 680                 685

Pro Leu Leu Lys Gln Gln Leu Lys Leu Ser Arg Leu
    690                 695                 700

<210> SEQ ID NO 3
<211> LENGTH: 1145
<212> TYPE: DNA
<213> ORGANISM: Zea mays
<220> FEATURE:
<221> NAME/KEY: CDS
<222> LOCATION: (1)..(1017)

<400> SEQUENCE: 3 att cgg ctc gag gtt cct ctt aag act gta aac agg cag tgc tct tct        48
Ile Arg Leu Glu Val Pro Leu Lys Thr Val Asn Arg Gln Cys Ser Ser
  1               5                  10                  15 ggc ctt cag gca gtt gca gat gtt gcc act gct att aaa gca ggg ctc        96
Gly Leu Gln Ala Val Ala Asp Val Ala Thr Ala Ile Lys Ala Gly Leu
             20                  25                  30 tat gac att ggt att gct gct ggt ttg gag tcc atg aca gtg aac aaa       144
Tyr Asp Ile Gly Ile Ala Ala Gly Leu Glu Ser Met Thr Val Asn Lys
         35                  40                  45 gtt agt ctt gat ggc caa gcg aat ccc aaa gtt gag ctg ttt tct caa       192
Val Ser Leu Asp Gly Gln Ala Asn Pro Lys Val Glu Leu Phe Ser Gln
     50                  55                  60 gca cgc gat tgt ctt ctc cca atg ggc ctc aca tct gag aat gtt gca       240
Ala Arg Asp Cys Leu Leu Pro Met Gly Leu Thr Ser Glu Asn Val Ala
 65                  70                  75                  80 cac cgt ttt ggc ata aca cga ctg gag caa gat caa gct gct gtt gag       288
His Arg Phe Gly Ile Thr Arg Leu Glu Gln Asp Gln Ala Ala Val Glu
                 85                  90                  95 tca cat aga aag gct gct gcc gca gca gct gct ggt aaa ttc aaa gag       336
Ser His Arg Lys Ala Ala Ala Ala Ala Ala Ala Gly Lys Phe Lys Glu
            100                 105                 110 gaa att gtg cca gtt cat aca aag att gtt gat cca aaa act ggt gag       384
Glu Ile Val Pro Val His Thr Lys Ile Val Asp Pro Lys Thr Gly Glu
        115                 120                 125 gaa aag aag atc gta gtc tct gca gat gat gga atc cga gtg gat act       432
Glu Lys Lys Ile Val Val Ser Ala Asp Asp Gly Ile Arg Val Asp Thr
    130                 135                 140 tct ctt gca gtc ctg tca aaa ctc aaa cca gca ttt tca aag gat ggc       480
Ser Leu Ala Val Leu Ser Lys Leu Lys Pro Ala Phe Ser Lys Asp Gly
145                 150                 155                 160 agc act act gct ggg aat gca agc caa gtg agt gat ggt gct ggg gcc       528
Ser Thr Thr Ala Gly Asn Ala Ser Gln Val Ser Asp Gly Ala Gly Ala
                165                 170                 175 gtc ttg cta atg aga cgg gat gtt gct atg aag aag ggt ctt cca gtt       576
Val Leu Leu Met Arg Arg Asp Val Ala Met Lys Lys Gly Leu Pro Val
            180                 185                 190 ctt ggt gtc ttt agg acc ttt gcc gct gtt gga gtt gat cca gct gta       624
```

```
                Leu Gly Val Phe Arg Thr Phe Ala Ala Val Gly Val Asp Pro Ala Val
                        195                 200                 205 atg ggt att ggt cct gcc gtt gca atc cct gca gca gtg aaa gct gct          672
Met Gly Ile Gly Pro Ala Val Ala Ile Pro Ala Ala Val Lys Ala Ala
    210                 215                 220 ggc ctt cag atg gat gat atc gat ctt ttc gaa atc aac gag gct ttt          720
Gly Leu Gln Met Asp Asp Ile Asp Leu Phe Glu Ile Asn Glu Ala Phe
225                 230                 235                 240 gca tct cag tat gtc tac tgc tgc aag aag ttg gaa ctt gat cct gct          768
Ala Ser Gln Tyr Val Tyr Cys Cys Lys Lys Leu Glu Leu Asp Pro Ala
                245                 250                 255 aaa gtc aat gtt aat ggc ggt gca atg gct ctt gga cat cct ttg ggt          816
Lys Val Asn Val Asn Gly Gly Ala Met Ala Leu Gly His Pro Leu Gly
                260                 265                 270 gct aca ggt gca cgg tgc gtc agt act ctt ctc aat gag atg aag cgc          864
Ala Thr Gly Ala Arg Cys Val Ser Thr Leu Leu Asn Glu Met Lys Arg
            275                 280                 285 cgc ggc aag gat tgc cgg ttc gga gtg att tct atg tgc ata ggt tct          912
Arg Gly Lys Asp Cys Arg Phe Gly Val Ile Ser Met Cys Ile Gly Ser
        290                 295                 300 ggg atg ggt gct gct gct gtg ttc gag cgg gga gac ggc gtt gat gag          960
Gly Met Gly Ala Ala Ala Val Phe Glu Arg Gly Asp Gly Val Asp Glu
305                 310                 315                 320 ctc acc aat gct cgg gga atc tcg acc cac aac tgg ctt tcc aag gac         1008
Leu Thr Asn Ala Arg Gly Ile Ser Thr His Asn Trp Leu Ser Lys Asp
                325                 330                 335 gcc atg taa agctacaccc accaaaattt gccggaactg gtagcattgt                  1057
Ala Met ttccagatcg ctgtagggag cgaattgggg aataaaatga ttttgtattt gtcgcccctg        1117
ctggggattt aaaaaaaaaa aaaaaagg                                           1145

<210> SEQ ID NO 4
<211> LENGTH: 338
<212> TYPE: PRT
<213> ORGANISM: Zea mays

<400> SEQUENCE: 4

Ile Arg Leu Glu Val Pro Leu Lys Thr Val Asn Arg Gln Cys Ser Ser
 1               5                  10                  15

Gly Leu Gln Ala Val Ala Asp Val Ala Thr Ala Ile Lys Ala Gly Leu
                20                  25                  30

Tyr Asp Ile Gly Ile Ala Ala Gly Leu Glu Ser Met Thr Val Asn Lys
            35                  40                  45

Val Ser Leu Asp Gly Gln Ala Asn Pro Lys Val Glu Leu Phe Ser Gln
        50                  55                  60

Ala Arg Asp Cys Leu Leu Pro Met Gly Leu Thr Ser Glu Asn Val Ala
 65                 70                  75                  80

His Arg Phe Gly Ile Thr Arg Leu Glu Gln Asp Gln Ala Ala Val Glu
                85                  90                  95

Ser His Arg Lys Ala Ala Ala Ala Ala Gly Lys Phe Lys Glu
            100                 105                 110

Glu Ile Val Pro Val His Thr Lys Ile Val Asp Pro Lys Thr Gly Glu
        115                 120                 125

Glu Lys Lys Ile Val Val Ser Ala Asp Asp Gly Ile Arg Val Asp Thr
130                 135                 140

Ser Leu Ala Val Leu Ser Lys Leu Lys Pro Ala Phe Ser Lys Asp Gly
145                 150                 155                 160
```

```
Ser Thr Thr Ala Gly Asn Ala Ser Gln Val Ser Asp Gly Ala Gly Ala
            165                 170                 175
Val Leu Leu Met Arg Arg Asp Val Ala Met Lys Lys Gly Leu Pro Val
            180                 185                 190
Leu Gly Val Phe Arg Thr Phe Ala Ala Val Gly Val Asp Pro Ala Val
            195                 200                 205
Met Gly Ile Gly Pro Ala Val Ala Ile Pro Ala Ala Val Lys Ala Ala
            210                 215                 220
Gly Leu Gln Met Asp Asp Ile Asp Leu Phe Glu Ile Asn Glu Ala Phe
225                 230                 235                 240
Ala Ser Gln Tyr Val Tyr Cys Cys Lys Lys Leu Glu Leu Asp Pro Ala
            245                 250                 255
Lys Val Asn Val Asn Gly Gly Ala Met Ala Leu Gly His Pro Leu Gly
            260                 265                 270
Ala Thr Gly Ala Arg Cys Val Ser Thr Leu Leu Asn Glu Met Lys Arg
            275                 280                 285
Arg Gly Lys Asp Cys Arg Phe Gly Val Ile Ser Met Cys Ile Gly Ser
290                 295                 300
Gly Met Gly Ala Ala Ala Val Phe Glu Arg Gly Asp Gly Val Asp Glu
305                 310                 315                 320
Leu Thr Asn Ala Arg Gly Ile Ser Thr His Asn Trp Leu Ser Lys Asp
            325                 330                 335
Ala Met

<210> SEQ ID NO 5
<211> LENGTH: 2254
<212> TYPE: DNA
<213> ORGANISM: Glycine max
<220> FEATURE:
<221> NAME/KEY: CDS
<222> LOCATION: (119)..(2116)

<400> SEQUENCE: 5
atgtttcatt cactcttcta accaaacccg aaaacagagt acaagatttt aaacacgcga      60
acaccgtgtt tgaaaatcga acataagagg agagggcgca atcgttaggg tttccaag      118 atg gaa ggc atg gtt gat cac ctg gct ttc gag cgg aac aat tcg cag      166
Met Glu Gly Met Val Asp His Leu Ala Phe Glu Arg Asn Asn Ser Gln
 1               5                  10                  15 ttc gat gtc gac gag atg aag atc gtt tgg gcc ggt tct cgt cac gct      214
Phe Asp Val Asp Glu Met Lys Ile Val Trp Ala Gly Ser Arg His Ala
            20                  25                  30 ttt gaa gta tct gac aaa atg gct cgc ctc gtt gcc agc gat ccg gca      262
Phe Glu Val Ser Asp Lys Met Ala Arg Leu Val Ala Ser Asp Pro Ala
        35                  40                  45 ttc aga aag gat gat aga gtt gtg ctt gat agg aag gct tta ttt aag      310
Phe Arg Lys Asp Asp Arg Val Val Leu Asp Arg Lys Ala Leu Phe Lys
    50                  55                  60 aac act ttg agg aaa gca gct tat gca tgg aaa agg att att gag ctc      358
Asn Thr Leu Arg Lys Ala Ala Tyr Ala Trp Lys Arg Ile Ile Glu Leu
65                  70                  75                  80 cgt ctc agt gaa gag gaa gct gct atg ctc aga tcc ttt gtg gac caa      406
Arg Leu Ser Glu Glu Glu Ala Ala Met Leu Arg Ser Phe Val Asp Gln
                85                  90                  95 cct gct ttt acg gat cta cat tgg gga atg ttt gtt cct gct atc aaa      454
Pro Ala Phe Thr Asp Leu His Trp Gly Met Phe Val Pro Ala Ile Lys
            100                 105                 110
```

```
gga caa gga act gag gaa cag cag aag aag tgg ttg cct ttg gct cat    502
Gly Gln Gly Thr Glu Glu Gln Gln Lys Lys Trp Leu Pro Leu Ala His
            115                 120                 125 aag atg caa ata att ggt tgt tat gcc caa act gaa ctt ggc cat gga    550
Lys Met Gln Ile Ile Gly Cys Tyr Ala Gln Thr Glu Leu Gly His Gly
        130                 135                 140 tct aat gtt caa ggg ctt gaa aca act gca acc ttt gat ccc aga aca    598
Ser Asn Val Gln Gly Leu Glu Thr Thr Ala Thr Phe Asp Pro Arg Thr
145                 150                 155                 160 gac gag ttt gta att cat agc ccc aca ttg act tca agc aaa tgg tgg    646
Asp Glu Phe Val Ile His Ser Pro Thr Leu Thr Ser Ser Lys Trp Trp
                165                 170                 175 cct ggt gga ttg ggt aaa gtg tca aca cat gcc gtg gtt tat gcc cga    694
Pro Gly Gly Leu Gly Lys Val Ser Thr His Ala Val Val Tyr Ala Arg
            180                 185                 190 cta att act gat ggc caa gat cat gga gtg cat ggt ttc att gtc cag    742
Leu Ile Thr Asp Gly Gln Asp His Gly Val His Gly Phe Ile Val Gln
        195                 200                 205 ctg cgg agc ctg gat gat cac tta cct ctt cca ggc ata act gtt ggt    790
Leu Arg Ser Leu Asp Asp His Leu Pro Leu Pro Gly Ile Thr Val Gly
210                 215                 220 gat att gga atg aaa ttt gga aat gga gca tat aac tcc atg gat aat    838
Asp Ile Gly Met Lys Phe Gly Asn Gly Ala Tyr Asn Ser Met Asp Asn
225                 230                 235                 240 ggg atg cta agg ttt gac cat gta cgg att cca aga aat caa atg tta    886
Gly Met Leu Arg Phe Asp His Val Arg Ile Pro Arg Asn Gln Met Leu
                245                 250                 255 atg agg gtt tca cag gta aca agg gaa gga aaa tat gta caa tcc agt    934
Met Arg Val Ser Gln Val Thr Arg Glu Gly Lys Tyr Val Gln Ser Ser
            260                 265                 270 gtt cca cga caa tta gtc tat ggt act atg gta tat gta aga caa aca    982
Val Pro Arg Gln Leu Val Tyr Gly Thr Met Val Tyr Val Arg Gln Thr
        275                 280                 285 att gta tct gat gcg tca gtt gct ttg tcg cga gca gtt tgc att gct    1030
Ile Val Ser Asp Ala Ser Val Ala Leu Ser Arg Ala Val Cys Ile Ala
290                 295                 300 aca aga tat agt gct gtt cga aga cag ttt ggg tca aaa gag gga ggt    1078
Thr Arg Tyr Ser Ala Val Arg Arg Gln Phe Gly Ser Lys Glu Gly Gly
305                 310                 315                 320 ctt gag aca cag gtg att gat tat aaa acg cag caa gct agg ctc ttc    1126
Leu Glu Thr Gln Val Ile Asp Tyr Lys Thr Gln Gln Ala Arg Leu Phe
                325                 330                 335 cct ttg tta gct tct gcc tat gcc ttc aga ttt gtt ggt gaa tgg ttg    1174
Pro Leu Leu Ala Ser Ala Tyr Ala Phe Arg Phe Val Gly Glu Trp Leu
            340                 345                 350 aaa tgg ctt tat atg gat gtg atg aaa aga ttg caa gcc agt gat ttt    1222
Lys Trp Leu Tyr Met Asp Val Met Lys Arg Leu Gln Ala Ser Asp Phe
        355                 360                 365 tca acc tta cct gag gct cat gcg tgc act gca ggg ttg aag tcc ttg    1270
Ser Thr Leu Pro Glu Ala His Ala Cys Thr Ala Gly Leu Lys Ser Leu
370                 375                 380 act act tca gca act gct gat gga att gag gaa tgc cgc aaa cta tgt    1318
Thr Thr Ser Ala Thr Ala Asp Gly Ile Glu Glu Cys Arg Lys Leu Cys
385                 390                 395                 400 ggt ggc cat ggt tac ctt tgc agc agt ggt ctc cct gag tta ttt gca    1366
Gly Gly His Gly Tyr Leu Cys Ser Ser Gly Leu Pro Glu Leu Phe Ala
                405                 410                 415 gtc tac att cct acc tgc aca tac gaa gga gac aac act gtg ctg ctt    1414
Val Tyr Ile Pro Thr Cys Thr Tyr Glu Gly Asp Asn Thr Val Leu Leu
            420                 425                 430
```

```
tta cag gtg gct agg cat ctc atc aag act att tct cag ttg ggc tcc    1462
Leu Gln Val Ala Arg His Leu Ile Lys Thr Ile Ser Gln Leu Gly Ser
            435                 440                 445 aga aac aag cct gtt ggt aca aca tct tac att gga cga gtg gaa cag    1510
Arg Asn Lys Pro Val Gly Thr Thr Ser Tyr Ile Gly Arg Val Glu Gln
        450                 455                 460 ctt atg caa tat cgt tct gat gtt cag aaa gtg gag gat tgg ctg aag    1558
Leu Met Gln Tyr Arg Ser Asp Val Gln Lys Val Glu Asp Trp Leu Lys
465                 470                 475                 480 cct aat gca gtg ttg gga gca ttt gaa gct agg gct gct aag aag gtg    1606
Pro Asn Ala Val Leu Gly Ala Phe Glu Ala Arg Ala Ala Lys Lys Val
                485                 490                 495 gtt gct tgt gct caa aat ctc agc aag ttt acc aat ccc gaa gaa ggt    1654
Val Ala Cys Ala Gln Asn Leu Ser Lys Phe Thr Asn Pro Glu Glu Gly
            500                 505                 510 ttc caa gaa ctc tca gtc gat cta gtt gag gca gct gtt gct cat tgc    1702
Phe Gln Glu Leu Ser Val Asp Leu Val Glu Ala Ala Val Ala His Cys
        515                 520                 525 cag tta att gtt gtt tcc aaa ttt att gag aag ttg cag caa gat atc    1750
Gln Leu Ile Val Val Ser Lys Phe Ile Glu Lys Leu Gln Gln Asp Ile
    530                 535                 540 cct gga aag gga gtg aaa cag caa tta gaa ctt ctt tgt agc att tac    1798
Pro Gly Lys Gly Val Lys Gln Gln Leu Glu Leu Leu Cys Ser Ile Tyr
545                 550                 555                 560 gct ttg ttt ctt ctt cac aag cat ttg ggt gat ttt ctt gca act ggc    1846
Ala Leu Phe Leu Leu His Lys His Leu Gly Asp Phe Leu Ala Thr Gly
                565                 570                 575 tgc atc act ccc aaa cag ggt tcc ctt gca aat gag ctg ctg agg tcc    1894
Cys Ile Thr Pro Lys Gln Gly Ser Leu Ala Asn Glu Leu Leu Arg Ser
            580                 585                 590 ttg tat tca cag gtt cgt cct aat gca att gca ctt gtt gat gcg ttt    1942
Leu Tyr Ser Gln Val Arg Pro Asn Ala Ile Ala Leu Val Asp Ala Phe
        595                 600                 605 aac tac act gat cac tac ctt ggt tcg gtt ctt ggt cgc tat gat gga    1990
Asn Tyr Thr Asp His Tyr Leu Gly Ser Val Leu Gly Arg Tyr Asp Gly
    610                 615                 620 gat gtg tat cca aag ctg tac gag gag gca tgg aag gat cca ttg aat    2038
Asp Val Tyr Pro Lys Leu Tyr Glu Glu Ala Trp Lys Asp Pro Leu Asn
625                 630                 635                 640 gat tca gtt gtg cca gat ggc ttc caa gaa tat att cga cca atg cta    2086
Asp Ser Val Val Pro Asp Gly Phe Gln Glu Tyr Ile Arg Pro Met Leu
                645                 650                 655 aag caa caa ctt cgt aat gct aga ctc taa attactttttt tataactgca    2136
Lys Gln Gln Leu Arg Asn Ala Arg Leu
            660                 665 ctgttgatac tggagaaagt tatgtattgc tttcaattta aaagacagta ataaagttct    2196
acgaaaggga aacaaatttg acatcaactt tgacaaaatt gattatgaat agaattga      2254

<210> SEQ ID NO 6
<211> LENGTH: 665
<212> TYPE: PRT
<213> ORGANISM: Glycine max

<400> SEQUENCE: 6

Met Glu Gly Met Val Asp His Leu Ala Phe Glu Arg Asn Asn Ser Gln
1               5                   10                  15

Phe Asp Val Asp Glu Met Lys Ile Val Trp Ala Gly Ser Arg His Ala
            20                  25                  30
```

-continued

```
Phe Glu Val Ser Asp Lys Met Ala Arg Leu Val Ala Ser Asp Pro Ala
     35                  40                  45

Phe Arg Lys Asp Asp Arg Val Val Leu Asp Arg Lys Ala Leu Phe Lys
 50                  55                  60

Asn Thr Leu Arg Lys Ala Ala Tyr Ala Trp Lys Arg Ile Ile Glu Leu
 65                  70                  75                  80

Arg Leu Ser Glu Glu Ala Ala Met Leu Arg Ser Phe Val Asp Gln
                 85                  90                  95

Pro Ala Phe Thr Asp Leu His Trp Gly Met Phe Val Pro Ala Ile Lys
             100                 105                 110

Gly Gln Gly Thr Glu Glu Gln Gln Lys Lys Trp Leu Pro Leu Ala His
             115                 120                 125

Lys Met Gln Ile Ile Gly Cys Tyr Ala Gln Thr Glu Leu Gly His Gly
     130                 135                 140

Ser Asn Val Gln Gly Leu Glu Thr Thr Ala Thr Phe Asp Pro Arg Thr
145                 150                 155                 160

Asp Glu Phe Val Ile His Ser Pro Thr Leu Thr Ser Ser Lys Trp Trp
                 165                 170                 175

Pro Gly Gly Leu Gly Lys Val Ser Thr His Ala Val Val Tyr Ala Arg
             180                 185                 190

Leu Ile Thr Asp Gly Gln Asp His Gly Val His Gly Phe Ile Val Gln
     195                 200                 205

Leu Arg Ser Leu Asp Asp His Leu Pro Leu Pro Gly Ile Thr Val Gly
     210                 215                 220

Asp Ile Gly Met Lys Phe Gly Asn Gly Ala Tyr Asn Ser Met Asp Asn
225                 230                 235                 240

Gly Met Leu Arg Phe Asp His Val Arg Ile Pro Arg Asn Gln Met Leu
                 245                 250                 255

Met Arg Val Ser Gln Val Thr Arg Glu Gly Lys Tyr Val Gln Ser Ser
             260                 265                 270

Val Pro Arg Gln Leu Val Tyr Gly Thr Met Val Tyr Val Arg Gln Thr
     275                 280                 285

Ile Val Ser Asp Ala Ser Val Ala Leu Ser Arg Ala Val Cys Ile Ala
     290                 295                 300

Thr Arg Tyr Ser Ala Val Arg Arg Gln Phe Gly Ser Lys Glu Gly Gly
305                 310                 315                 320

Leu Glu Thr Gln Val Ile Asp Tyr Lys Thr Gln Gln Ala Arg Leu Phe
                 325                 330                 335

Pro Leu Leu Ala Ser Ala Tyr Ala Phe Arg Phe Val Gly Glu Trp Leu
             340                 345                 350

Lys Trp Leu Tyr Met Asp Val Met Lys Arg Leu Gln Ala Ser Asp Phe
     355                 360                 365

Ser Thr Leu Pro Glu Ala His Ala Cys Thr Ala Gly Leu Lys Ser Leu
     370                 375                 380

Thr Thr Ser Ala Thr Ala Asp Gly Ile Glu Glu Cys Arg Lys Leu Cys
385                 390                 395                 400

Gly Gly His Gly Tyr Leu Cys Ser Ser Gly Leu Pro Glu Leu Phe Ala
                 405                 410                 415

Val Tyr Ile Pro Thr Cys Thr Tyr Glu Gly Asp Asn Thr Val Leu Leu
             420                 425                 430

Leu Gln Val Ala Arg His Leu Ile Lys Thr Ile Ser Gln Leu Gly Ser
     435                 440                 445

Arg Asn Lys Pro Val Gly Thr Thr Ser Tyr Ile Gly Arg Val Glu Gln
```

```
                     450                   455                    460
Leu Met Gln Tyr Arg Ser Asp Val Gln Lys Val Glu Asp Trp Leu Lys
465                 470                    475                 480

Pro Asn Ala Val Leu Gly Ala Phe Glu Ala Arg Ala Ala Lys Lys Val
                485                    490                 495

Val Ala Cys Ala Gln Asn Leu Ser Lys Phe Thr Asn Pro Glu Glu Gly
            500                    505                 510

Phe Gln Glu Leu Ser Val Asp Leu Val Glu Ala Val Ala His Cys
            515                    520                 525

Gln Leu Ile Val Val Ser Lys Phe Ile Glu Lys Leu Gln Gln Asp Ile
        530                    535                 540

Pro Gly Lys Gly Val Lys Gln Gln Leu Glu Leu Leu Cys Ser Ile Tyr
545                 550                    555                 560

Ala Leu Phe Leu Leu His Lys His Leu Gly Asp Phe Leu Ala Thr Gly
                565                    570                 575

Cys Ile Thr Pro Lys Gln Gly Ser Leu Ala Asn Glu Leu Leu Arg Ser
            580                    585                 590

Leu Tyr Ser Gln Val Arg Pro Asn Ala Ile Ala Leu Val Asp Ala Phe
        595                    600                 605

Asn Tyr Thr Asp His Tyr Leu Gly Ser Val Leu Gly Arg Tyr Asp Gly
        610                    615                 620

Asp Val Tyr Pro Lys Leu Tyr Glu Glu Ala Trp Lys Asp Pro Leu Asn
625                 630                    635                 640

Asp Ser Val Val Pro Asp Gly Phe Gln Glu Tyr Ile Arg Pro Met Leu
                645                    650                 655

Lys Gln Gln Leu Arg Asn Ala Arg Leu
                660                    665

<210> SEQ ID NO 7
<211> LENGTH: 1651
<212> TYPE: DNA
<213> ORGANISM: Glycine max
<220> FEATURE:
<221> NAME/KEY: CDS
<222> LOCATION: (48)..(1439)

<400> SEQUENCE: 7
gcttcttctt tcttttttc aatttccaaa tcacgaaact caagaag atg gag aaa       56
                                                  Met Glu Lys
                                                   1 gcg atc aac aga cag aag att ttg ctt cat cat ctc aac cct tca tca    104
Ala Ile Asn Arg Gln Lys Ile Leu Leu His His Leu Asn Pro Ser Ser
  5                  10                  15 tcc acc cac ccc aac gaa tca tcc tcc ctc cat gct tca gca tgt gtg    152
Ser Thr His Pro Asn Glu Ser Ser Ser Leu His Ala Ser Ala Cys Val
 20                  25                  30                  35 gcg ggg gat agc gct gct tat caa agg aca tcg aca ttc ggg gac gat    200
Ala Gly Asp Ser Ala Ala Tyr Gln Arg Thr Ser Thr Phe Gly Asp Asp
             40                  45                  50 gtt gtg atc gtg gct gct tat cgg act gct cat tgc aaa gct aaa cga    248
Val Val Ile Val Ala Ala Tyr Arg Thr Ala His Cys Lys Ala Lys Arg
         55                  60                  65 ggt ggt ttc aaa gac act ctt cct gat gat cca ctg gct cct gtt ttg    296
Gly Gly Phe Lys Asp Thr Leu Pro Asp Asp Pro Leu Ala Pro Val Leu
     70                  75                  80 aag gct gta att gag aaa acc aat gtg aac cca agt gaa gtt ggg gat    344
Lys Ala Val Ile Glu Lys Thr Asn Val Asn Pro Ser Glu Val Gly Asp
 85                  90                  95
```

| | | |
|---|---|---|
| att gtt gta ggt agt gta ttg gct cct gga gct caa aga gct agt gaa<br>Ile Val Val Gly Ser Val Leu Ala Pro Gly Ala Gln Arg Ala Ser Glu<br>100                          105                        110                      115 | | 392 |
| tgc cga atg gct gca ttt tat gct ggt ttt ccc gaa act gtg cct gtt<br>Cys Arg Met Ala Ala Phe Tyr Ala Gly Phe Pro Glu Thr Val Pro Val<br>                    120                        125                        130 | | 440 |
| agg acc gtt aat agg caa tgt tca tct ggg ctc cag gct gtc gct gat<br>Arg Thr Val Asn Arg Gln Cys Ser Ser Gly Leu Gln Ala Val Ala Asp<br>              135                        140                        145 | | 488 |
| gta gct gct gct ata agg gct ggg ttc tat gac att ggt att ggt gcc<br>Val Ala Ala Ala Ile Arg Ala Gly Phe Tyr Asp Ile Gly Ile Gly Ala<br>                  150                        155                        160 | | 536 |
| ggt ttg gaa tct atg acc act aat cca atg gga tgg gat gga tca gtg<br>Gly Leu Glu Ser Met Thr Thr Asn Pro Met Gly Trp Asp Gly Ser Val<br>165                          170                        175 | | 584 |
| aat cct aag gta aaa atg ttt gaa caa gca caa aac tgc ctt ctt cct<br>Asn Pro Lys Val Lys Met Phe Glu Gln Ala Gln Asn Cys Leu Leu Pro<br>180                          185                        190                        195 | | 632 |
| atg gga att acc tct gaa aat gtt gca cag cgc ttt ggg gtt tca agg<br>Met Gly Ile Thr Ser Glu Asn Val Ala Gln Arg Phe Gly Val Ser Arg<br>              200                        205                        210 | | 680 |
| aag gaa caa gac cag gct gca gtt gag tct cac agg cga gct gct gca<br>Lys Glu Gln Asp Gln Ala Ala Val Glu Ser His Arg Arg Ala Ala Ala<br>                  215                        220                        225 | | 728 |
| gct act gct gct ggt aaa ttt aaa gat gaa att gtc cca gtt acc acc<br>Ala Thr Ala Ala Gly Lys Phe Lys Asp Glu Ile Val Pro Val Thr Thr<br>              230                        235                        240 | | 776 |
| aag att gtg gac cca aaa acc ggt gag gag aaa tct gtc acc att tct<br>Lys Ile Val Asp Pro Lys Thr Gly Glu Glu Lys Ser Val Thr Ile Ser<br>245                          250                        255 | | 824 |
| gtt gat gat gga att cga cct ggc aca aca gtg tct gat cta gga aga<br>Val Asp Asp Gly Ile Arg Pro Gly Thr Thr Val Ser Asp Leu Gly Arg<br>260                          265                        270                        275 | | 872 |
| ctc aaa cct gtg ttc aag aaa gac gga agc acc act gct ggt aat tct<br>Leu Lys Pro Val Phe Lys Lys Asp Gly Ser Thr Thr Ala Gly Asn Ser<br>              280                        285                        290 | | 920 |
| agc cag gtg acc gat ggg gct tca gct gtt ctg ctg atg aaa aga agt<br>Ser Gln Val Thr Asp Gly Ala Ser Ala Val Leu Leu Met Lys Arg Ser<br>                  295                        300                        305 | | 968 |
| gtt gca ttg caa aag ggg cta ccc att ctt ggt gta ttc agg act ttt<br>Val Ala Leu Gln Lys Gly Leu Pro Ile Leu Gly Val Phe Arg Thr Phe<br>              310                        315                        320 | | 1016 |
| gca gca gtt ggt gtt gat cct gcc atc atg ggt gtt ggc cct gct gct<br>Ala Ala Val Gly Val Asp Pro Ala Ile Met Gly Val Gly Pro Ala Ala<br>325                          330                        335 | | 1064 |
| gca att cct gtt gct gtt aag gct gca ggt cta gag ctt gat gat att<br>Ala Ile Pro Val Ala Val Lys Ala Ala Gly Leu Glu Leu Asp Asp Ile<br>340                          345                        350                        355 | | 1112 |
| gat ctt ttt gaa ata aat gag gca ttt gcc tcc cag ttc gtg tat tgc<br>Asp Leu Phe Glu Ile Asn Glu Ala Phe Ala Ser Gln Phe Val Tyr Cys<br>                  360                        365                        370 | | 1160 |
| cgt aac aag cta ggg ctt gat cca gaa aag atc aat gtt aat gga ggt<br>Arg Asn Lys Leu Gly Leu Asp Pro Glu Lys Ile Asn Val Asn Gly Gly<br>              375                        380                        385 | | 1208 |
| gca atg gca att ggg cat cct ctg ggt tca aca ggt gct cga tgt gtt<br>Ala Met Ala Ile Gly His Pro Leu Gly Ser Thr Gly Ala Arg Cys Val<br>              390                        395                        400 | | 1256 |
| gca act ctg ttg cat gaa atg aag aaa cgt ggc agg gac tgt cga ttt<br>Ala Thr Leu Leu His Glu Met Lys Lys Arg Gly Arg Asp Cys Arg Phe | | 1304 |

-continued

```
                     405                 410                 415
gga gtt ata tct atg tgc ata ggt act gga atg ggg gca gct gct gtt         1352
Gly Val Ile Ser Met Cys Ile Gly Thr Gly Met Gly Ala Ala Ala Val
420                 425                 430                 435 ttt gag agt ggt gat tgt gct gat gag cta tgc aat gcc cgg aaa gtg         1400
Phe Glu Ser Gly Asp Cys Ala Asp Glu Leu Cys Asn Ala Arg Lys Val
                440                 445                 450 gat gac ctt ctt tta tcc aag gat gct cgc ttg aaa tag ttacttcata          1449
Asp Asp Leu Leu Leu Ser Lys Asp Ala Arg Leu Lys
                455                 460 ctcactatat ttggtcatca ataagaaat cacaataaag tcttttttcta tggtagtgat       1509 aatgtcaacc actcctcaag cgtttaatcc tttctactta ttagacttgc attaatttgt       1569
gatatatttt ggacaattgt aaacatacac ttaattttc ttctatatct ttttcactcc       1629
aaaaaaaaaa aaaaaaaaaa aa                                                1651

<210> SEQ ID NO 8
<211> LENGTH: 463
<212> TYPE: PRT
<213> ORGANISM: Glycine max

<400> SEQUENCE: 8

Met Glu Lys Ala Ile Asn Arg Gln Lys Ile Leu Leu His His Leu Asn
 1               5                  10                  15

Pro Ser Ser Thr His Pro Asn Glu Ser Ser Ser Leu His Ala Ser
            20                  25                  30

Ala Cys Val Ala Gly Asp Ser Ala Ala Tyr Gln Arg Thr Ser Thr Phe
        35                  40                  45

Gly Asp Asp Val Val Ile Val Ala Ala Tyr Arg Thr Ala His Cys Lys
    50                  55                  60

Ala Lys Arg Gly Gly Phe Lys Asp Thr Leu Pro Asp Asp Pro Leu Ala
65                  70                  75                  80

Pro Val Leu Lys Ala Val Ile Glu Lys Thr Asn Val Asn Pro Ser Glu
                85                  90                  95

Val Gly Asp Ile Val Val Gly Ser Val Leu Ala Pro Gly Ala Gln Arg
            100                 105                 110

Ala Ser Glu Cys Arg Met Ala Ala Phe Tyr Ala Gly Phe Pro Glu Thr
        115                 120                 125

Val Pro Val Arg Thr Val Asn Arg Gln Cys Ser Ser Gly Leu Gln Ala
    130                 135                 140

Val Ala Asp Val Ala Ala Ala Ile Arg Ala Gly Phe Tyr Asp Ile Gly
145                 150                 155                 160

Ile Gly Ala Gly Leu Glu Ser Met Thr Thr Asn Pro Met Gly Trp Asp
                165                 170                 175

Gly Ser Val Asn Pro Lys Val Lys Met Phe Glu Gln Ala Gln Asn Cys
            180                 185                 190

Leu Leu Pro Met Gly Ile Thr Ser Glu Asn Val Ala Gln Arg Phe Gly
        195                 200                 205

Val Ser Arg Lys Glu Gln Asp Gln Ala Ala Val Glu Ser His Arg Arg
    210                 215                 220

Ala Ala Ala Thr Ala Ala Gly Lys Phe Lys Asp Glu Ile Val Pro
225                 230                 235                 240

Val Thr Thr Lys Ile Val Asp Pro Lys Thr Gly Glu Glu Lys Ser Val
                245                 250                 255

Thr Ile Ser Val Asp Asp Gly Ile Arg Pro Gly Thr Thr Val Ser Asp
```

```
                 260                  265                  270
Leu Gly Arg Leu Lys Pro Val Phe Lys Lys Asp Gly Ser Thr Thr Ala
            275                  280                  285
Gly Asn Ser Ser Gln Val Thr Asp Gly Ala Ser Val Leu Leu Met
        290                  295                  300
Lys Arg Ser Val Ala Leu Gln Lys Gly Leu Pro Ile Leu Gly Val Phe
305                  310                  315                  320
Arg Thr Phe Ala Ala Val Gly Val Asp Pro Ala Ile Met Gly Val Gly
                325                  330                  335
Pro Ala Ala Ile Pro Val Ala Val Lys Ala Ala Gly Leu Glu Leu
            340                  345                  350
Asp Asp Ile Asp Leu Phe Glu Ile Asn Glu Ala Phe Ala Ser Gln Phe
            355                  360                  365
Val Tyr Cys Arg Asn Lys Leu Gly Leu Asp Pro Glu Lys Ile Asn Val
    370                  375                  380
Asn Gly Gly Ala Met Ala Ile Gly His Pro Leu Gly Ser Thr Gly Ala
385                  390                  395                  400
Arg Cys Val Ala Thr Leu Leu His Glu Met Lys Lys Arg Gly Arg Asp
                405                  410                  415
Cys Arg Phe Gly Val Ile Ser Met Cys Ile Gly Thr Gly Met Gly Ala
                420                  425                  430
Ala Ala Val Phe Glu Ser Gly Asp Cys Ala Asp Glu Leu Cys Asn Ala
            435                  440                  445
Arg Lys Val Asp Asp Leu Leu Leu Ser Lys Asp Ala Arg Leu Lys
    450                  455                  460

<210> SEQ ID NO 9
<211> LENGTH: 2263
<212> TYPE: DNA
<213> ORGANISM: Glycine max
<220> FEATURE:
<221> NAME/KEY: CDS
<222> LOCATION: (140)..(2134)

<400> SEQUENCE: 9
agagaaaaat ggggtggcaa agggacctac taagttttat aacccagaga tccatgctgc    60
tgcattctgt ctgtaacaca atacaatcat cattcatcaa atcactgaaa ccaaagccac   120
aagctgcgac atcagaaga atg gaa gac ggt gtt gac cac ttg gct ttc gag   172
                    Met Glu Asp Gly Val Asp His Leu Ala Phe Glu
                      1               5                  10 agg aac aag gcg cag ttc gat gtt gag gac atg aaa atc att tgg gcc   220
Arg Asn Lys Ala Gln Phe Asp Val Glu Asp Met Lys Ile Ile Trp Ala
             15                  20                  25 ggt tct cgt caa gac ttt gag ctt tcg gat cga att tct cgc ctt gtt   268
Gly Ser Arg Gln Asp Phe Glu Leu Ser Asp Arg Ile Ser Arg Leu Val
         30                  35                  40 gcc agc gat ccg gcg ttc aga aag gat gat aga aca cgc ttg ata gga   316
Ala Ser Asp Pro Ala Phe Arg Lys Asp Asp Arg Thr Arg Leu Ile Gly
     45                  50                  55 aga ttg ttt aaa aac acc ttg aga aaa gca gct tat gca tgg aaa agg   364
Arg Leu Phe Lys Asn Thr Leu Arg Lys Ala Ala Tyr Ala Trp Lys Arg
 60                  65                  70                  75 atc aac gag ctc cgt ctt aat gaa cag gaa gct tat aag ctc aga tct   412
Ile Asn Glu Leu Arg Leu Asn Glu Gln Glu Ala Tyr Lys Leu Arg Ser
                 80                  85                  90 ttt gtg gat caa cct gca ttt acg gat ctt cat tgg gga atg ttt gtg   460
Phe Val Asp Gln Pro Ala Phe Thr Asp Leu His Trp Gly Met Phe Val
```

-continued

| | | | | 95 | | | | | 100 | | | | | 105 | | | |
|---|---|---|---|---|---|---|---|---|---|---|---|---|---|---|---|---|---|
| cct | gct | atc | caa | gga | caa | ggc | act | gac | gaa | cag | cag | cag | aag | tgg | ttg | | 508 |
| Pro | Ala | Ile | Gln | Gly | Gln | Gly | Thr | Asp | Glu | Gln | Gln | Gln | Lys | Trp | Leu | | |
| | | 110 | | | | | 115 | | | | | 120 | | | | | |
| cct | cta | gct | tat | ggg | atg | caa | ata | att | ggt | tgc | tat | gcc | caa | act | gaa | | 556 |
| Pro | Leu | Ala | Tyr | Gly | Met | Gln | Ile | Ile | Gly | Cys | Tyr | Ala | Gln | Thr | Glu | | |
| | 125 | | | | | 130 | | | | | 135 | | | | | | |
| ctg | ggt | cat | ggg | tcc | aat | gtt | caa | ggg | cta | gaa | aca | act | gca | acg | ttt | | 604 |
| Leu | Gly | His | Gly | Ser | Asn | Val | Gln | Gly | Leu | Glu | Thr | Thr | Ala | Thr | Phe | | |
| 140 | | | | | 145 | | | | | 150 | | | | | 155 | | |
| gat | ccc | aaa | aca | gac | gaa | ttt | gtt | atc | cat | agc | ccc | aca | ttg | act | tcc | | 652 |
| Asp | Pro | Lys | Thr | Asp | Glu | Phe | Val | Ile | His | Ser | Pro | Thr | Leu | Thr | Ser | | |
| | | | 160 | | | | | 165 | | | | | 170 | | | | |
| agc | aaa | tgg | tgg | cct | ggt | gga | ttg | ggt | aaa | ata | tcc | acc | cat | gct | gtt | | 700 |
| Ser | Lys | Trp | Trp | Pro | Gly | Gly | Leu | Gly | Lys | Ile | Ser | Thr | His | Ala | Val | | |
| | | 175 | | | | | 180 | | | | | 185 | | | | | |
| gct | tat | gcc | cgt | cta | att | att | ggt | ggt | gaa | gac | cat | gga | gtg | cat | ggt | | 748 |
| Ala | Tyr | Ala | Arg | Leu | Ile | Ile | Gly | Gly | Glu | Asp | His | Gly | Val | His | Gly | | |
| | 190 | | | | | 195 | | | | | 200 | | | | | | |
| ttc | atc | gtc | cag | ctg | cgg | agc | ttg | gat | gat | cac | ttg | cct | ctt | cca | ggc | | 796 |
| Phe | Ile | Val | Gln | Leu | Arg | Ser | Leu | Asp | Asp | His | Leu | Pro | Leu | Pro | Gly | | |
| 205 | | | | | 210 | | | | | 215 | | | | | | | |
| ata | act | att | ggt | gat | att | ggg | atg | aaa | ttt | gga | aat | gca | gct | tat | aac | | 844 |
| Ile | Thr | Ile | Gly | Asp | Ile | Gly | Met | Lys | Phe | Gly | Asn | Ala | Ala | Tyr | Asn | | |
| 220 | | | | | 225 | | | | | 230 | | | | | 235 | | |
| acc | atg | gac | aat | gga | gtt | cta | aga | ttt | gac | cat | gta | cga | att | cca | agg | | 892 |
| Thr | Met | Asp | Asn | Gly | Val | Leu | Arg | Phe | Asp | His | Val | Arg | Ile | Pro | Arg | | |
| | | | 240 | | | | | 245 | | | | | 250 | | | | |
| aat | caa | atg | tta | atg | agg | gtt | tca | cag | gtt | acc | aga | gaa | gga | aga | tat | | 940 |
| Asn | Gln | Met | Leu | Met | Arg | Val | Ser | Gln | Val | Thr | Arg | Glu | Gly | Arg | Tyr | | |
| | | 255 | | | | | 260 | | | | | 265 | | | | | |
| gta | agc | tca | aat | gtt | cca | aga | caa | tta | gtt | tat | ggt | act | atg | gta | aat | | 988 |
| Val | Ser | Ser | Asn | Val | Pro | Arg | Gln | Leu | Val | Tyr | Gly | Thr | Met | Val | Asn | | |
| | 270 | | | | | 275 | | | | | 280 | | | | | | |
| gtg | aga | cag | aaa | atc | gta | gct | gat | gca | tca | gtt | gct | ttg | tct | cga | gca | | 1036 |
| Val | Arg | Gln | Lys | Ile | Val | Ala | Asp | Ala | Ser | Val | Ala | Leu | Ser | Arg | Ala | | |
| | 285 | | | | | 290 | | | | | 295 | | | | | | |
| gtt | tgc | att | gct | aca | aga | tat | agt | gct | gtt | aga | aga | cag | ttt | gga | tca | | 1084 |
| Val | Cys | Ile | Ala | Thr | Arg | Tyr | Ser | Ala | Val | Arg | Arg | Gln | Phe | Gly | Ser | | |
| 300 | | | | | 305 | | | | | 310 | | | | | 315 | | |
| cat | aat | gga | ggt | cta | gaa | aca | cag | gtg | att | gat | tac | aaa | aca | cag | cag | | 1132 |
| His | Asn | Gly | Gly | Leu | Glu | Thr | Gln | Val | Ile | Asp | Tyr | Lys | Thr | Gln | Gln | | |
| | | | 320 | | | | | 325 | | | | | 330 | | | | |
| gct | agg | ctc | ttc | cct | ttg | ctg | gct | tct | gct | tat | gct | ttc | aga | ttt | gtg | | 1180 |
| Ala | Arg | Leu | Phe | Pro | Leu | Leu | Ala | Ser | Ala | Tyr | Ala | Phe | Arg | Phe | Val | | |
| | | 335 | | | | | 340 | | | | | 345 | | | | | |
| ggt | ggg | tgg | ctg | aaa | tgg | ctt | tat | atg | gat | gtg | acg | gaa | aga | ttg | caa | | 1228 |
| Gly | Gly | Trp | Leu | Lys | Trp | Leu | Tyr | Met | Asp | Val | Thr | Glu | Arg | Leu | Gln | | |
| | 350 | | | | | 355 | | | | | 360 | | | | | | |
| gct | aat | gat | ttt | tca | aca | ttg | cct | gag | gct | cat | gca | tgc | act | gct | gga | | 1276 |
| Ala | Asn | Asp | Phe | Ser | Thr | Leu | Pro | Glu | Ala | His | Ala | Cys | Thr | Ala | Gly | | |
| | 365 | | | | | 370 | | | | | 375 | | | | | | |
| ttg | aaa | tcc | ttg | act | act | aca | gca | act | gct | gat | gga | att | gaa | gaa | tgc | | 1324 |
| Leu | Lys | Ser | Leu | Thr | Thr | Thr | Ala | Thr | Ala | Asp | Gly | Ile | Glu | Glu | Cys | | |
| 380 | | | | | 385 | | | | | 390 | | | | | 395 | | |
| cgt | aaa | cta | tgt | ggt | ggt | cat | ggt | tac | ctt | tgt | agc | agt | ggt | ctc | cct | | 1372 |
| Arg | Lys | Leu | Cys | Gly | Gly | His | Gly | Tyr | Leu | Cys | Ser | Ser | Gly | Leu | Pro | | |
| | | | 400 | | | | | 405 | | | | | 410 | | | | |
| gag | tta | ttt | gct | gtt | tat | gtt | cct | gcc | tgc | acg | tat | gaa | gga | gac | aat | | 1420 |

```
                Glu Leu Phe Ala Val Tyr Val Pro Ala Cys Thr Tyr Glu Gly Asp Asn
                            415                 420                 425 gtt gtg ctt ctg tta cag gtg gca agg cat ctc atg aag act gtt tct        1468
Val Val Leu Leu Leu Gln Val Ala Arg His Leu Met Lys Thr Val Ser
            430                 435                 440 cag ctg ggc tct gga aat aag ccc gtt ggt act aca gct tat atg gct        1516
Gln Leu Gly Ser Gly Asn Lys Pro Val Gly Thr Thr Ala Tyr Met Ala
445                 450                 455 cga gtg gaa caa ctg atg caa tat cac tct gat gtt gaa aag gct gag        1564
Arg Val Glu Gln Leu Met Gln Tyr His Ser Asp Val Glu Lys Ala Glu
460                 465                 470                 475 gat tgg ttg aag cct aat gta gtg ttg gaa gca ttt gaa gct agg gct        1612
Asp Trp Leu Lys Pro Asn Val Val Leu Glu Ala Phe Glu Ala Arg Ala
                480                 485                 490 tct agg atg tca gtt gct tgt gct caa aat ctt agc aag ttt gct aac        1660
Ser Arg Met Ser Val Ala Cys Ala Gln Asn Leu Ser Lys Phe Ala Asn
            495                 500                 505 cct gaa gag ggt ttt caa gaa cta gct gct gat tta gtt gat gcc gcg        1708
Pro Glu Glu Gly Phe Gln Glu Leu Ala Ala Asp Leu Val Asp Ala Ala
            510                 515                 520 gtt gct cat tgc cag tta att gtt gtt tcc aaa ttt att gag aag ttg        1756
Val Ala His Cys Gln Leu Ile Val Val Ser Lys Phe Ile Glu Lys Leu
525                 530                 535 cag caa gat ata cct gga aag gga gtg aaa aag caa tta gaa gtt ctt        1804
Gln Gln Asp Ile Pro Gly Lys Gly Val Lys Lys Gln Leu Glu Val Leu
540                 545                 550                 555 tgc agc att tat gct ttg ttt cta ctt cat aaa cat ctg ggt gat ttt        1852
Cys Ser Ile Tyr Ala Leu Phe Leu Leu His Lys His Leu Gly Asp Phe
                560                 565                 570 ctt tcc act ggc tgc att aac cca aaa caa gga tca ctt gca agt gag        1900
Leu Ser Thr Gly Cys Ile Asn Pro Lys Gln Gly Ser Leu Ala Ser Glu
            575                 580                 585 cag ctg aga aac tta tat tca cag gtc cgt cct aat gca att gcg ctt        1948
Gln Leu Arg Asn Leu Tyr Ser Gln Val Arg Pro Asn Ala Ile Ala Leu
            590                 595                 600 gtt gat gca ttt aac tac act gat cac tac ctt ggt tca att ctt gga        1996
Val Asp Ala Phe Asn Tyr Thr Asp His Tyr Leu Gly Ser Ile Leu Gly
605                 610                 615 cgt tac gat gga aat gtg tat ccg aag atg aac gag gag gca tgg aag        2044
Arg Tyr Asp Gly Asn Val Tyr Pro Lys Met Asn Glu Glu Ala Trp Lys
620                 625                 630                 635 gat cct ttg aat gat tca gtt gtt cct gat ggc ttt aaa gag tat att        2092
Asp Pro Leu Asn Asp Ser Val Val Pro Asp Gly Phe Lys Glu Tyr Ile
                640                 645                 650 caa ccg atg ctt aag cag caa cta cgt aat gct agg ctg tag            2134
Gln Pro Met Leu Lys Gln Gln Leu Arg Asn Ala Arg Leu
            655                 660 ttaattttgt ggcaatgatg cttttggcat ctaagaaatt tacccagact attctgattt   2194
acaactctta ataaagttgt gtttgccagc tagtaattac catcgcaatt aggtgtatct   2254
ggaactgga                                                           2263
```

<210> SEQ ID NO 10
<211> LENGTH: 664
<212> TYPE: PRT
<213> ORGANISM: Glycine max

<400> SEQUENCE: 10

Met Glu Asp Gly Val Asp His Leu Ala Phe Glu Arg Asn Lys Ala Gln
1               5                   10                  15

```
Phe Asp Val Glu Asp Met Lys Ile Ile Trp Ala Gly Ser Arg Gln Asp
            20                  25                  30
Phe Glu Leu Ser Asp Arg Ile Ser Arg Leu Val Ala Ser Asp Pro Ala
        35                  40                  45
Phe Arg Lys Asp Asp Arg Thr Arg Leu Ile Gly Arg Leu Phe Lys Asn
    50                  55                  60
Thr Leu Arg Lys Ala Ala Tyr Ala Trp Lys Arg Ile Asn Glu Leu Arg
65                  70                  75                  80
Leu Asn Glu Gln Glu Ala Tyr Lys Leu Arg Ser Phe Val Asp Gln Pro
                85                  90                  95
Ala Phe Thr Asp Leu His Trp Gly Met Phe Val Pro Ala Ile Gln Gly
            100                 105                 110
Gln Gly Thr Asp Glu Gln Gln Gln Lys Trp Leu Pro Leu Ala Tyr Gly
        115                 120                 125
Met Gln Ile Ile Gly Cys Tyr Ala Gln Thr Glu Leu Gly His Gly Ser
    130                 135                 140
Asn Val Gln Gly Leu Glu Thr Thr Ala Thr Phe Asp Pro Lys Thr Asp
145                 150                 155                 160
Glu Phe Val Ile His Ser Pro Thr Leu Thr Ser Ser Lys Trp Trp Pro
                165                 170                 175
Gly Gly Leu Gly Lys Ile Ser Thr His Ala Val Ala Tyr Ala Arg Leu
            180                 185                 190
Ile Ile Gly Gly Glu Asp His Gly Val His Gly Phe Ile Val Gln Leu
        195                 200                 205
Arg Ser Leu Asp Asp His Leu Pro Leu Pro Gly Ile Thr Ile Gly Asp
    210                 215                 220
Ile Gly Met Lys Phe Gly Asn Ala Ala Tyr Asn Thr Met Asp Asn Gly
225                 230                 235                 240
Val Leu Arg Phe Asp His Val Arg Ile Pro Arg Asn Gln Met Leu Met
                245                 250                 255
Arg Val Ser Gln Val Thr Arg Glu Gly Arg Tyr Val Ser Ser Asn Val
            260                 265                 270
Pro Arg Gln Leu Val Tyr Gly Thr Met Val Asn Val Arg Gln Lys Ile
        275                 280                 285
Val Ala Asp Ala Ser Val Ala Leu Ser Arg Ala Val Cys Ile Ala Thr
    290                 295                 300
Arg Tyr Ser Ala Val Arg Arg Gln Phe Gly Ser His Asn Gly Gly Leu
305                 310                 315                 320
Glu Thr Gln Val Ile Asp Tyr Lys Thr Gln Gln Ala Arg Leu Phe Pro
                325                 330                 335
Leu Leu Ala Ser Ala Tyr Ala Phe Arg Phe Val Gly Gly Trp Leu Lys
            340                 345                 350
Trp Leu Tyr Met Asp Val Thr Glu Arg Leu Gln Ala Asn Asp Phe Ser
        355                 360                 365
Thr Leu Pro Glu Ala His Ala Cys Thr Ala Gly Leu Lys Ser Leu Thr
    370                 375                 380
Thr Thr Ala Thr Ala Asp Gly Ile Glu Glu Cys Arg Lys Leu Cys Gly
385                 390                 395                 400
Gly His Gly Tyr Leu Cys Ser Ser Gly Leu Pro Glu Leu Phe Ala Val
                405                 410                 415
Tyr Val Pro Ala Cys Thr Tyr Glu Gly Asp Asn Val Val Leu Leu Leu
            420                 425                 430
```

```
Gln Val Ala Arg His Leu Met Lys Thr Val Ser Gln Leu Gly Ser Gly
            435                 440                 445

Asn Lys Pro Val Gly Thr Thr Ala Tyr Met Ala Arg Val Glu Gln Leu
    450                 455                 460

Met Gln Tyr His Ser Asp Val Glu Lys Ala Glu Asp Trp Leu Lys Pro
465                 470                 475                 480

Asn Val Val Leu Glu Ala Phe Glu Ala Arg Ala Ser Arg Met Ser Val
                485                 490                 495

Ala Cys Ala Gln Asn Leu Ser Lys Phe Ala Asn Pro Glu Glu Gly Phe
            500                 505                 510

Gln Glu Leu Ala Ala Asp Leu Val Asp Ala Ala Val Ala His Cys Gln
            515                 520                 525

Leu Ile Val Val Ser Lys Phe Ile Glu Lys Leu Gln Gln Asp Ile Pro
        530                 535                 540

Gly Lys Gly Val Lys Lys Gln Leu Glu Val Leu Cys Ser Ile Tyr Ala
545                 550                 555                 560

Leu Phe Leu Leu His Lys His Leu Gly Asp Phe Leu Ser Thr Gly Cys
                565                 570                 575

Ile Asn Pro Lys Gln Gly Ser Leu Ala Ser Glu Gln Leu Arg Asn Leu
            580                 585                 590

Tyr Ser Gln Val Arg Pro Asn Ala Ile Ala Leu Val Asp Ala Phe Asn
        595                 600                 605

Tyr Thr Asp His Tyr Leu Gly Ser Ile Leu Gly Arg Tyr Asp Gly Asn
        610                 615                 620

Val Tyr Pro Lys Met Asn Glu Glu Ala Trp Lys Asp Pro Leu Asn Asp
625                 630                 635                 640

Ser Val Val Pro Asp Gly Phe Lys Glu Tyr Ile Gln Pro Met Leu Lys
            645                 650                 655

Gln Gln Leu Arg Asn Ala Arg Leu
            660
```

NUCLEIC ACID MOLECULES AND OTHER MOLECULES ASSOCIATED WITH THE β-OXIDATION PATHWAY

FIELD OF THE INVENTION

The present invention is in the field of plant biochemistry, particularly as it pertains to the β-oxidation pathway. More specifically, the invention relates to nucleic acid molecules that encode proteins and fragments of proteins associated with the β-oxidation pathway, the proteins and fragments of proteins so encoded, and antibodies capable of binding the proteins. The invention also relates to methods of using the nucleic acid molecules, proteins, and fragments of proteins.

BACKGROUND OF THE INVENTION

The degradation of fatty acids occurs by the β-oxidation pathway. β-oxidation plays an important role in the metabolism of stored seed lipids during seed germination and early seedling growth (Cooper and Beevers, *J. Biol. Chem.*, 244:3514–3520 (1969)). The end-products of lipid breakdown provide energy to the growing seedling until it becomes photosynthetic. β-oxidation is not, however, restricted to the seedling growth stage of plant development. This process occurs in several different tissues and its possible physiological roles include energy generation, turnover of membrane lipids and the removal of toxic fatty acids (Gerhardt, *Physiol. Veg.*, 24:397–410 (1986); Tramantano et al., *Phytochemistry* 36:19–21 (1994)). It also plays a role in membrane turnover during senescence (Wanner et al., *Plant Sci.*, 78:199–206 (1991)). Therefore, β-oxidation is a consistent basic function of all cells of a plant (Gerhardt, *Planta* 159:238–246 (1983)).

Fatty acid oxidation is reported in three systems; mitochondrial, peroxisomal and bacterial. Mitochondrial and peroxisomal β-oxidation occurs in animal cells, peroxisomal β-oxidation occurs in plant cells and bacterial β-oxidation is reported to differ from eukaryotic β-oxidation. Peroxisomal β-oxidation is similar to the mitochondrial β-oxidation, except that carnitine has not been reported to be required. In mitochondria, long chain fatty acids are activated by acyl-CoA synthetase on the mitochondrial outer membrane and acyl groups of the CoA esters are transported into the matrix by carnitine acyltransferase. Mitochondrial β-oxidation has been reported as cyclic repetition of four basic reactions catalyzed by a long, medium and short chain acyl-CoA dehydrogenase, an enoyl-CoA hydratase, a 3-hydroxyacyl CoA dehydrogenase and 3-ketoacyl-CoA thiolase. The reported substrates of β-oxidation enzymes are coenzyme A (CoA) derivatives of fatty acid. In peroxisomes, fatty acids have been reported to be activated by acyl-CoA synthetase (Shindo and Hashimoto, *J. Biochem.* 84:1177–1181 (1978); Krisans et al., *J. Biol. Chem.* 255:9599–9607 (1980). Acyl-CoA esters have been reported to be degraded by β-oxidation cycle. β-oxidation has been reported to be catalyzed by acyl-CoA oxidase, enoyl CoA isomerase/enoyl-CoA hydratase/3-hydroxylacyl-CoA dehydrogenase.

Acyl-CoA oxidase (EC 1.3.3.6) is the first reported enzyme of the fatty acid β-oxidation pathway. This enzyme catalyzes the desaturation of acyl-CoAs longer than eight carbons to 2-trans-enoyl-CoAs, by donating electrons directly to molecular oxygen and releasing $H_2O_2$ (Lazarow et al., 1976). Acyl-CoA oxidase substrate has been reported as acyl moieties of more than eight carbon atoms (Osumi et al., *J. Biochem.* 87:1735–1746 (1980).

Bifunctional protein enoyl-CoA hydratase/3-hydroxyacyl-CoA dehydrogenase is the second reported enzyme of the peroxisomal β-oxidation pathway. Enoyl-CoA hydratase catalyzes hydration of double bond to form 3-L-hydroxyacyl-CoA. 3-hydroxyacyl-CoA dehydrogenase catalyzes $NAD^+$ dependent dehydrogenation of β-hydroxyacyl-CoA resulting in the formation of the corresponding β-ketoacyl-CoA. Originally, bifunctional protein enoyl-CoA hydratase/3-hydroxyacyl-CoA dehydrogenase was reported in rat liver as a monomeric protein with two enzyme activities (Osumi and Hashimoto, *Biochem. Biophys. Res. Commun.* 89:580–584 (1979). Enoyl-CoA hydratase/3-hydroxyacyl-CoA dehydrogenase has also been reported as a trifunctional protein with an enoyl-CoA isomerase activity in addition to hydratase and dehydrogenase activity (Palorassi and Hiltunen, *J. Biol. Chem.* 265:2446–2449 (1990). Enoyl CoA isomerase/enoyl-CoA hydratase/3-hydroxylacyl-CoA dehydrogenase has also been reported in bovine liver, pig heart and human liver (Fong and Schulz, *Methods Enzymol.* 71:390–398 (1981); Furuta et al., *J. Biochem.* 88:1059–1070 (1980); Reddy et al., *Proc. Natl. Acad. Sci.* (*USA*) 84:3214–3218 (1987); Osumi and Hashimoto, *J. Biol. Chem.* 262: 8138–8143 (1979). Rat enoyl-CoA hydratase/3-hydroxyacyl-CoA dehydrogenase/enoyl-CoA isomerase has been reported to contain seven exons. Exons one through five, are reported at the amino terminal to constitute a hydratase domain. 3-hydroxyacyl CoA dehydrogenase activity is reported in exons six and seven. 3-hydroxyacyl CoA dehydrogenase activity has been reported to be present in a 722 amino acid polypeptide (Ishii et al, *J. Biol. Chem.* 262:8144–8150 (1987); Osumi et al., *J. Biol. Chem.* 260:8905–8910 (1985).

3-Ketoacyl-CoA thiolase is reported to catalyze the last step of fatty acid β-oxidation, resulting in Cα-Cβ cleavage yielding acetyl-CoA and new acyl-CoA with two fewer carbons the original one. Two types of mitochondrial thiolases have been reported which differ chain length specificity: 3-ketoacyl CoA thiolase (also known as thiolase I) and acetoacetyl-CoA thiolase (EC 2.3.1.9) (also known as thiolase II). 3-Ketoacyl-CoA-thiolase (EC 2.3.1.16) has reported activity on substrates ranging from acetoacetyl-CoA to long-chain 3-ketoacyl-CoAs at low concentration (Middleton, *Methods Enzymol.* 35:128–136 (1975; Staack et al, *J. Biol. Chem.* 253:1827–1931 (1978). Thiolase has been reported as a tetramer. Rat mitochondrial 3-ketoacyl-CoA thiolase has been reported to have a molecular weight of 41866 Kd (Arakawa et al, *EMBO J.* 6:1361–1366 (1987). Peroxisomal 3-ketoacyl-CoA thiolase has been reported in rat liver as a homodimer with a molecular mass of 89 kDa.

Mitochondrial 3-ketoacyl-CoA thiolases and mitochondrial and cytosolic acetoacetyl-CoA specific thiolases have been reported as homotetramers, each subunit is about 40 kDa (Miyazawa et al., *Eur. J. Biochem.* 103:589–596 (1980). Genes encoding these enzymes have been reported (Hijikata et al., *J. Biol. Chem.* 262:8151–8158 (1990). A rat peroxisomal 3-ketoacyl-CoA thiolase and a mitochondrial 3-ketoacyl-CoA thiolase have been reported which contain cysteine residues that are important for substrate binding (Hijikata et al., *J. Biol. Chem.* 262:8151–8158 (1987); Arakawa et al., *EMBO J.* 6:1361–1366 (1987)). Thiolases from different species have been reported to have an essential sulfhydryl serving as an acyl acceptor during the thiolytic cleavage (Gilbert et al., *J. Biol. Chem.* 256:7371–7377 (1981).

The isolation and identification of cDNAs encoding proteins in the β-oxidation pathway will help to confirm the activities of the enzymes encoded and their substrate specificities. Expression studies may be used, for example, to determine fatty acid substrate chain length specificity. There are multiple isozymes of acyl-CoA oxidase and these isozymes show specificity towards short, medium and long chain fatty acyl-CoAs (Hooks et al., *Biochem J.*, 320:607–614 (1996); Hooks et al., *Plant J.*, 20:1–13 (1999)). It is likely that long chain specificity may be required for β-oxidation of seed lipids and broad specificity may be required for other stages.

The present invention provides complete and partial cDNAs encoding β-oxidation pathway enzymes. The invention also provides protein and fragment molecules with amino acid sequences in the β-oxidation pathway. The nucleic acid molecules, drawn from soy and maize, may be used to understand the different functions of b-oxidation during plant growth and development, leading to the development of nutritionally and agriculturally enhanced crops and products.

SUMMARY OF THE INVENTION

The present invention includes and provides a substantially purified nucleic acid molecule comprising a nucleic acid sequence selected from SEQ ID NO: 1, SEQ ID NO: 3, SEQ ID NO: 5, SEQ ID NO: 7 or SEQ ID NO: 9 or complements thereof or fragments of either.

The present invention further provides a substantially purified soybean or maize β-oxidation pathway enzyme, or fragment thereof encoded by a nucleic acid sequence which specifically hybridizes to a nucleic acid molecule comprising a nucleic acid sequence selected from the group consisting of a complement of SEQ ID NO: 1, SEQ ID NO: 3, SEQ ID NO: 5, SEQ ID NO: 7 or SEQ ID NO: 9.

The present invention also provides a substantially purified protein or fragment thereof comprising an amino acid sequence selected from the group consisting of SEQ ID NO: 2, SEQ ID NO: 4, SEQ ID NO: 6, SEQ ID NO: 8 or SEQ ID NO: 10 or fragment thereof.

The present invention also provides a substantially purified protein or fragment thereof encoded by a nucleic acid molecule comprising a nucleic acid sequence selected from the group consisting of SEQ ID NO: 1, SEQ ID NO: 3, SEQ ID NO: 5, SEQ ID NO: 7 or SEQ ID NO: 9.

The present invention further provides a purified antibody or fragment thereof which is capable of specifically binding to a protein or fragment thereof, wherein the protein or fragment thereof comprises an amino acid sequence selected from the group consisting of SEQ ID NO: 2, SEQ ID NO: 4, SEQ ID NO: 6, SEQ ID NO: 8 or SEQ ID NO: 10.

The present invention also provides a transformed plant having a nucleic acid molecule which comprises: (A) an exogenous promoter region which functions in a plant cell to cause the production of a mRNA molecule; (B) a structural nucleic acid molecule encoding a protein or fragment thereof comprising an amino acid sequence selected from the group consisting of SEQ ID NO: 2, SEQ ID NO: 4, SEQ ID NO: 6, SEQ ID NO: 8 or SEQ ID NO: 10 or fragment thereof; and (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a transcribed nucleic acid molecule with a transcribed strand and a non-transcribed strand, wherein the transcribed strand is complementary to a nucleic acid molecule encoding a protein or fragment thereof comprising an amino acid sequence selected from the group consisting of SEQ ID NO: 2, SEQ ID NO: 4, SEQ ID NO: 6, SEQ ID NO: 8 or SEQ ID NO: 10 or fragment thereof; which is linked to (C) a 3' non-translated sequence that functions in plant cells to cause termination of transcription and addition of polyadenylated ribonucleotides to a 3' end of the mRNA molecule.

The present invention also provides a method for determining a level or pattern of a beta-oxidation pathway enzyme in a plant cell or plant tissue comprising: (A) incubating, under conditions permitting nucleic acid hybridization, a marker nucleic acid molecule, the marker nucleic acid molecule selected from the group of marker nucleic acid molecules which specifically hybridize to a nucleic acid molecule having the nucleic acid sequence selected from the group consisting of SEQ ID NO: 1, SEQ ID NO: 3, SEQ ID NO: 5 SEQ ID NO: 7 or SEQ ID NO: 9 or complements thereof or fragments of either, with a complementary nucleic acid molecule obtained from the plant cell or plant tissue, wherein nucleic acid hybridization between the marker nucleic acid molecule and the complementary nucleic acid molecule obtained from the plant cell or plant tissue permits the detection of an mRNA for the enzyme; (B) permitting hybridization between the marker nucleic acid molecule and the complementary nucleic acid molecule obtained from the plant cell or plant tissue; and (C) detecting the level or pattern of the complementary nucleic acid, wherein the detection of the complementary nucleic acid is predictive of the level or pattern of the beta-oxidation pathway enzyme.

The present invention also provides a method for determining the level or pattern of a beta-oxidation pathway enzyme in a plant cell or plant tissue comprising: (A) incubating under conditions permitting nucleic acid hybridization: a marker nucleic acid molecule, the marker nucleic acid molecule comprising a nucleotide sequence selected from the group consisting of SEQ ID NO: 1, SEQ ID NO: 3, SEQ ID NO: 5 SEQ ID NO: 7 or SEQ ID NO: 9 or complements thereof, with a complementary nucleic acid molecule obtained from a plant cell or plant tissue, wherein nucleic acid hybridization between the marker nucleic acid molecule, and the complementary nucleic acid molecule obtained from the plant cell or plant tissue permits the detection of said beta-oxidation pathway enzyme; (B) permitting hybridization between the marker nucleic acid molecule and the complementary nucleic acid molecule obtained from the plant cell or plant tissue; and (C) detecting the level or pattern of the complementary nucleic acid, wherein the detection of said complementary nucleic acid is predictive of the level or pattern of the beta-oxidation pathway enzyme.

The present invention provides a method of determining a mutation in a plant whose presence is predictive of a mutation affecting a level or pattern of a protein comprising the steps: (A) incubating, under conditions permitting nucleic acid hybridization, a marker nucleic acid, the marker nucleic acid selected from the group of marker nucleic acid molecules which specifically hybridize to a nucleic acid molecule having a nucleic acid sequence selected from the group of SEQ ID NO: 1, SEQ ID NO: 3, SEQ ID NO: 5 SEQ ID NO: 7 or SEQ ID NO: 9 or complements thereof and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the protein in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method of producing a plant containing an overexpressed protein comprising: (A) transforming the plant with a functional nucleic acid molecule, wherein the functional nucleic acid molecule comprises a promoter region, wherein the promoter region is linked to a structural region, wherein the structural region comprises a nucleic acid sequence encoding an amino acid sequence selected from the group consisting of SEQ ID NO: 2, SEQ ID NO: 4, SEQ ID NO: 6, SEQ ID NO: 8 or SEQ ID NO: 10 or fragment thereof wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the protein; and (B) growing the transformed plant.

The present invention also provides a method of producing a plant containing reduced levels of a beta-oxidation pathway enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule encoding an amino acid sequence consisting of SEQ ID NO: 2, SEQ ID NO: 4, SEQ ID NO: 6, SEQ ID NO: 8 or SEQ ID NO: 10 or fragment thereof; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in co-suppression of the beta-oxidation pathway enzyme; and (B) growing the transformed plant.

The present invention also provides a method for reducing expression of a beta-oxidation pathway enzyme in a plant comprising: (A) transforming the plant with a nucleic acid molecule, the nucleic acid molecule having an exogenous promoter region which functions in a plant cell to cause the production of a mRNA molecule, wherein the exogenous promoter region is linked to a transcribed nucleic acid molecule having a transcribed strand and a non-transcribed strand, wherein the transcribed strand is complementary to a nucleic acid molecule having a nucleic acid sequence that encodes a protein having an amino acid sequence selected from the group consisting of SEQ ID NO: 2, SEQ ID NO: 4, SEQ ID NO: 6, SEQ ID NO: 8 or SEQ ID NO: 10 or fragments thereof and the transcribed strand is complementary to an endogenous mRNA molecule; and wherein the transcribed nucleic acid molecule is linked to a 3' non-translated sequence that functions in the plant cell to cause termination of transcription and addition of polyadenylated ribonucleotides to a 3' end of a mRNA molecule; and (B) growing the transformed plant.

The present invention also provides a method of determining an association between a polymorphism and a plant trait comprising: (A) hybridizing a nucleic acid molecule specific for the polymorphism to genetic material of a plant, wherein the nucleic acid molecule has a nucleic acid sequence selected from the group consisting of SEQ ID NO: 1, SEQ ID NO: 3, SEQ ID NO: 5, SEQ ID NO: 7 or SEQ ID NO: or complements thereof or fragment of either; and (B) calculating the degree of association between the polymorphism and the plant trait.

The present invention also provides a method of isolating a nucleic acid that encodes a beta-oxidation pathway enzyme or fragment thereof comprising: (A) incubating under conditions permitting nucleic acid hybridization, a first nucleic acid molecule comprising a nucleic acid sequence selected from the group consisting of SEQ ID NO: 1, SEQ ID NO: 3, SEQ ID NO: 5 SEQ ID NO: 7 or SEQ ID NO: 9 or complements thereof or fragment of either with a complementary second nucleic acid molecule obtained from a plant cell or plant tissue; (B) permitting hybridization between the first nucleic acid molecule and the second nucleic acid molecule obtained from the plant cell or plant tissue; and (C) isolating the second nucleic acid molecule.

The present invention also provides a method of analyzing the differences in the RNA profiles from more than one physiological source, said method comprising: a) obtaining a sample of ribonucleic acids from each of the physiological sources; b) generating a population of labeled nucleic acids for each of the physiological sources from said sample of ribonucleic acids; c) hybridizing the labeled nucleic acids for each of the physiological sources to an array of nucleic acid molecules stably associated with the surface of a substrate to produce a hybridization pattern for each of the physiological sources; said stably associated nucleic acid molecules selected from the group consisting of SEQ ID NO: 1, SEQ ID NO: 3, SEQ ID NO: 5, SEQ ID NO: 7 or SEQ ID NO:9 or fragments thereof and d) comparing the hybridization patterns for each of the different physiological sources.

The present invention provides soybean and maize nucleic acid molecules for use as molecular tags to isolate genetic regions (i.e. promoters and flanking sequences), isolate genes, map genes, and determine gene function. The present invention further provides soybean and maize nucleic acid molecules for use in determining if genes are members of a particular gene family.

DETAILED DESCRIPTION OF THE INVENTION

One skilled in the art can refer to general reference texts for detailed descriptions of known techniques discussed herein or equivalent techniques. These texts include *Current Protocols in Molecular Biology* Ausubel, et al., eds., John Wiley & Sons, N. Y. (1989), and supplements through September (1998), *Molecular Cloning, A Laboratory Manual*, Sambrook et al, $2^{nd}$ Ed., Cold Spring Harbor Press, Cold Spring Harbor, N.Y. (1989), *Genome Analysis: A Laboratory Manual 1: Analyzing DNA*, Birren et al., Cold Spring Harbor Press, Cold Spring Harbor, N.Y. (1997); *Genome Analysis: A Laboratory Manual 2: Detecting Genes*, Birren et al., Cold Spring Harbor Press, Cold Spring Harbor, N.Y. (1998); *Genome Analysis: A Laboratory Manual 3: Cloning Systems*, Birren et al., Cold Spring Harbor Press, Cold Spring Harbor, N.Y. (1999); *Genome Analysis: A Laboratory Manual 4: Mapping Genomes*, Birren et al., Cold Spring Harbor Press, Cold Spring Harbor, N.Y. (1999); Plant Molecular Biology: A Laboratory Manual, Clark, Springer-Verlag, Berlin, (1997), *Methods in Plant Molecular Biology*, Maliga et al., Cold Spring Harbor Press, Cold Spring Harbor, N.Y. (1995). These texts can, of course, also be referred to in making or using an aspect of the invention. It is understood that any of the agents of the invention can be substantially purified and/or be biologically active and/or recombinant.

Agents

The agents of the invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The term "substantially purified", as used herein, refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the invention may also be recombinant. As used herein, the term recombinant means any agent (e.g. DNA, peptide etc.), that is, or results, however indirect, from human manipulation of a nucleic acid molecule.

It is understood that the agents of the invention may be labeled with reagents that facilitate detection of the agent (e.g. fluorescent labels, Prober et al., *Science* 238:336–340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448). It is further understood that the invention provides recombinant bacterial, mammalian, microbial, archaebacterial, insect, fungal, algal, and plant cells as well as viral constructs comprising the agents of the invention.

(a) Nucleic Acid Molecules

Agents of the invention include nucleic acid molecules and, more preferably, nucleic acid molecules of maize, soybean or teosinte. In addition, a number of different plants can be the ultimate source of the nucleic acid molecules of the invention. The type or strain of plant may not be particularly important, but an exemplary group of maize genotypes includes: B73 (Illinois Foundation Seeds, Champaign, Ill. U.S.A.); B73×Mo17 (Illinois Foundation Seeds, Champaign, Ill. U.S.A.); DK604 (Dekalb Genetics, Dekalb, Ill. U.S.A.); H99 (Illinois Foundation Seeds, Champaign, Ill. U.S.A.); RX601 (Asgrow Seed Company, Des Moines, Iowa); and Mo17 (Illinois Foundation Seeds, Champaign, Ill. U.S.A.). An exemplary group of soybean genotypes includes: Asgrow 3244 (Asgrow Seed Company, Des Moines, Iowa U.S.A.) and BW211S Null (Tohoku University, Morioka, Japan). An exemplary group of teosinte includes *Zea mays* L. ssp *mexicana*.

In one aspect of the present invention, the nucleic acid molecules have one or more of the nucleic acid sequences set forth in SEQ ID NO: 1, SEQ ID NO: 3, SEQ ID NO: 5 SEQ ID NO: 7 or SEQ ID NO: 9 or complements thereof or fragments of either.

One subset of the nucleic acid molecules of the invention is fragment nucleic acids molecules. Fragment nucleic acid molecules may consist of significant portion(s) of, or indeed most of, the nucleic acid molecules of the invention, such as those specifically disclosed. Alternatively, the fragments may comprise smaller oligonucleotides (having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues).

A fragment of one or more of the nucleic acid molecules of the invention may be a probe and specifically a PCR probe. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (www-genome.wi.mit.edu/cgi-bin/primer/primer3.cgi), STSPipeline (www-genome.wi.mit.edu/cgi-bin/www-STS_Pipeline), or GeneUp (Pesole et al., BioTechniques 25:112–123 (1998)), for example, can be used to identify potential PCR primers.

Another subset of the nucleic acid molecules of the invention include nucleic acid molecules that encode a protein or fragment thereof.

A particularly preferred embodiment of the nucleic acid molecules of the present invention are plant nucleic acid molecules that comprise a nucleic acid sequence which encodes a maize or soybean ketoacyl thiolase or fragment thereof, more preferably a nucleic acid molecule comprising a nucleic acid selected from the group consisting of SEQ ID NO: 3 through SEQ ID NO: 7 or a nucleic acid molecule comprising a nucleic acid sequence which encodes ketoacyl thiolase or fragment thereof comprising an amino acid selected from the group consisting of SEQ ID: NO: 4 through SEQ ID NO: 8.

A particularly preferred embodiment of the nucleic acid molecules of the present invention are plant nucleic acid molecules that comprise a nucleic acid sequence which encodes a soybean or maize acyl-CoA oxidase or fragment thereof, more preferably a nucleic acid molecule comprising nucleic acid SEQ ID NO: 1, SEQ ID NO: 5 and SEQ ID NO: 9 or a nucleic acid molecule comprising a nucleic acid sequence which encodes an acyl-CoA oxidase or fragment thereof comprising amino acid SEQ ID: NO: 2 SEQ ID NO: 6 and SEQ ID NO: 10.

Nucleic acid molecules or fragments thereof of the present invention are capable of specifically hybridizing to other nucleic acid molecules under certain circumstances. Nucleic acid molecules of the present invention include those that specifically hybridize to nucleic acid molecules having a nucleic acid sequence selected from the group consisting of SEQ ID NO: 1, SEQ ID NO: 3, SEQ ID NO: 5 SEQ ID NO: 7 or SEQ ID NO: 9 or complements thereof.

As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning, A Laboratory Manual*, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology,* John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NO: 1, SEQ ID NO: 3, SEQ ID NO: 5 SEQ ID NO: 7 or SEQ ID NO: 9 or complements thereof under moderately stringent conditions, for example at about 2.0×SSC and about 65° C.

In a particularly preferred embodiment, a nucleic acid of the present invention will include those nucleic acid molecules that specifically hybridize to one or more of the nucleic acid molecules set forth in SEQ ID NO: 1 through SEQ ID NO: 5 or complements thereof under high stringency conditions such as 0.2×SSC and about 65° C.

In one aspect of the present invention, the nucleic acid molecules of the present invention have one or more of the nucleic acid sequences set forth in SEQ ID NO: 1, SEQ ID NO: 3, SEQ ID NO: 5 SEQ ID NO: 7 or SEQ ID NO: 9 or complements thereof. In another aspect of the present invention, one or more of the nucleic acid molecules of the present invention share between 100% and 90% sequence identity with one or more of the nucleic acid sequences set forth in SEQ ID NO: 1, SEQ ID NO: 3, SEQ ID NO: 5 SEQ ID NO: 7 or SEQ ID NO: 9 or complements thereof. In a further aspect of the present invention, one or more of the nucleic acid molecules of the present invention share between 100% and 95% sequence identity with one or more of the nucleic acid sequences set forth in SEQ ID NO: 1, SEQ ID NO: 3, SEQ ID NO: 5 SEQ ID NO: 7 or SEQ ID NO: 9 or complements thereof. In a more preferred aspect of the present invention, one or more of the nucleic acid molecules of the present invention share between 100% and 98% sequence identity with one or more of the nucleic acid sequences set forth in SEQ ID NO: 1, SEQ ID NO: 3, SEQ ID NO: 5 SEQ ID NO: 7 or SEQ ID NO: 9 or complements thereof. In an even more preferred aspect of the present invention, one or more of the nucleic acid molecules of the present invention share between 100% and 99% sequence identity with one or more of the sequences set forth in SEQ ID NO: 1, SEQ ID NO: 3, SEQ ID NO: 5 SEQ ID NO: 7 or SEQ ID NO: 9 or complements thereof.

Nucleic acid molecules of the present invention can comprise sequences that encode a protein or fragment thereof. In a preferred aspect of the present invention the nucleic acid molecules encode an amino acid sequence consisting of SEQ ID: 2, SEQ ID: 4, SEQ ID: 6, SEQ ID: 8, and SEQ ID: 10 or fragment thereof.

Nucleic acid molecules of the present invention also include homologues. Particularly preferred homologues are selected from the group consisting of alfalfa, Arabidopsis, barley, Brassica, broccoli, cabbage, citrus, cotton, garlic, oat, oilseed rape, onion, canola, flax, an ornamental plant, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, maize, and Phaseolus. In a preferred embodiment, nucleic acid molecules having in SEQ ID NO: 1, SEQ ID NO: 3, SEQ ID NO: 5 SEQ ID NO: 7 or SEQ ID NO: 9 or complements thereof and fragments of either can be utilized to obtain such homologues.

In another further aspect of the present invention, nucleic acid molecules of the present invention can comprise sequences, which differ from those encoding a protein or fragment thereof in SEQ ID: 2, SEQ ID: 4, SEQ ID: 6, SEQ ID: 8, and SEQ ID: 10 due to fact that the different nucleic acid sequence encodes a protein having one or more conservative amino acid changes. It is understood that codons capable of coding for such conservative amino acid substitutions are known in the art.

It is well known in the art that one or more amino acids in a native sequence can be substituted with another amino acid(s), the charge and polarity of which are similar to that of the native amino acid, i.e., a conservative amino acid substitution, resulting in a silent change. Conserved substitutes for an amino acid within the native polypeptide sequence can be selected from other members of the class to which the naturally occurring amino acid belongs. Amino acids can be divided into the following four groups: (1) acidic amino acids, (2) basic amino acids, (3) neutral polar amino acids, and (4) neutral nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid changes within the native polypeptides sequence can be made by substituting one amino acid within one of these groups with another amino acid within the same group. Biologically functional equivalents of the proteins or fragments thereof of the present invention can have ten or fewer conservative amino acid changes, more preferably seven or fewer conservative amino acid changes, and most preferably five or fewer conservative amino acid changes. The encoding nucleotide sequence will thus have corresponding base substitutions, permitting it to encode biologically functional equivalent forms of the proteins or fragments of the present invention.

It is understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, obtain a protein with like properties. It is thus contemplated by the inventors that various changes may be made in the peptide sequences of the proteins or fragments of the present invention, or corresponding DNA sequences that encode said peptides, without appreciable loss of their biological utility or activity. It is understood that codons capable of coding for such amino acid changes are known in the art.

In making such changes, the hydropathic index of amino acids may be considered. The importance of the hydropathic amino acid index in conferring interactive biological function on a protein is generally understood in the art (Kyte and Doolittle, *J. Mol. Biol.* 157, 105–132 (1982)). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, *J. Mol. Biol.* 157, 105–132 (1982)); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as govern by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within ±2 is preferred, those which are within ±1 are particularly preferred, and those within ±0.5 are even more particularly preferred.

In a further aspect of the present invention, one or more of the nucleic acid molecules of the present invention differ in nucleic acid sequence from those encoding a protein or fragment thereof set forth in SEQ ID: 1, SEQ ID: 3, SEQ ID: 5, SEQ ID: 7, and SEQ ID: 9 or fragment thereof due to the fact that one or more codons encoding an amino acid has been substituted for a codon that encodes a nonessential substitution of the amino acid originally encoded.

Agents of the invention include nucleic acid molecules that encode at least about a contiguous 10 amino acid region of a protein of the present invention, more preferably at least about a contiguous 25, 40, 50, 100, or 125 amino acid region of a protein of the present invention. In a preferred embodiment the protein is selected from the group consisting of a plant, more preferably a maize or soybean (a) ketoacyl-thiolase or fragment thereof, a plant, more preferably a soybean or maize acyl-CoA oxidase.

A nucleic acid molecule of the invention can also encode a homologue protein. As used herein, a homologue protein molecule or fragment thereof is a counterpart protein molecule or fragment thereof in a second species (e.g., maize acyl CoA oxidase is a homologue of Arabidopsis acyl CoA oxidase). A homologue can also be generated by molecular evolution or DNA shuffling techniques, so that the molecule retains at least one functional or structure characteristic of the original protein (see, for example, U.S. Pat. No. 5,811,238).

(b) Protein and Peptide Molecules

A class of agents includes one or more of the protein or fragments thereof or peptide molecules having a nucleic acid sequence selected from the group consisting of SEQ ID: 1, SEQ ID: 3, SEQ ID: 5, SEQ ID: 7, and SEQ ID: 9 or one or more of the protein or fragment thereof and peptide molecules encoded by other nucleic acid agents of the invention. A particular preferred class of proteins are those having an amino acid sequence selected from the group consisting of SEQ ID: 2, SEQ ID: 4, SEQ ID: 6, SEQ ID: 8, and SEQ ID: 10 or fragments thereof.

As used herein, the term "protein molecule" or "peptide molecule" includes any molecule that comprises five or more amino acids. It is well known in the art that proteins may undergo modification, including post-translational modifications, such as, but not limited to, disulfide bond formation, glycosylation, phosphorylation, or oligomerization. Thus, as used herein, the term "protein molecule" or "peptide molecule" includes any protein molecule that is modified by any biological or non-biological process. The terms "amino acid" and "amino acids" refer to all naturally occurring L-amino acids. This definition is meant to include norleucine, norvaline, ornithine, homocysteine, and homoserine.

One or more of the protein or fragment of peptide molecules may be produced via chemical synthesis, or more preferably, by expressing in a suitable bacterial or eukaryotic host. Suitable methods for expression are described by Sambrook et al., In: *Molecular Cloning, A Laboratory Manual*, 2nd Edition, Cold Spring Harbor Press, Cold Spring Harbor, N.Y. (1989), or similar texts.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin, etc.). Fusion protein or peptide molecules of the invention are preferably produced via recombinant means.

Another class of agents comprise protein or peptide molecules or fragments or fusions thereof comprising SEQ ID: 2, SEQ ID: 4, SEQ ID: 6, SEQ ID: 8, and SEQ ID: 10 or fragment thereof or encoded by SEQ ID: 1, SEQ ID: 3, SEQ ID: 5, SEQ ID: 7, and SEQ ID: 9 in which conservative, non-essential or non-relevant amino acid residues have been added, replaced or deleted. Computerized means for designing modifications in protein structure are known in the art (Dahiyat and Mayo, *Science* 278:82–87 (1997)).

Protein molecules of the present invention also include homologues. Particularly preferred homologues are selected from the group consisting of alfalfa, Arabidopsis, barley, Brassica, broccoli, cabbage, citrus, cotton, garlic, oat, oilseed rape, onion, canola, flax, an ornamental plant, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, maize, soybean, and Phaseolus.

In a preferred embodiment, nucleic acid molecules having SEQ ID: 1, SEQ ID: 3, SEQ ID: 5, SEQ ID: 7, and SEQ ID:

9 or complements and fragments of either can be utilized to obtain such homologues.

The degeneracy of the genetic code, which allows different nucleic acid sequences to code for the same protein or peptide, is known in the literature (U.S. Pat. No. 4,757,006).

In another further aspect of the present invention, one or more of the protein molecules of the present invention differ in protein sequence from those set forth in SEQ ID: 2, SEQ ID: 4, SEQ ID: 6, SEQ ID: 8, and SEQ ID: 10 or fragment thereof due to fact that the different protein encodes a protein having one or more conservative amino acid residue. In a further aspect of the present invention, one or more of the protein molecules of the present invention differ in protein sequence from those set forth in SEQ ID: 2, SEQ ID: 4, SEQ ID: 6, SEQ ID: 8, and SEQ ID: 10 or fragment thereof due to the fact that one or more codons encoding an amino acid has been substituted for a codon that encodes a nonessential substitution of the amino acid originally encoded.

Agents of the invention include proteins comprising at least about a contiguous 10 amino acid region preferably comprising at least about a contiguous 20 amino acid region, even more preferably comprising at least a contiguous 25, 35, 50, 75 or 100 amino acid region of a protein or fragment thereof of the present invention. In another preferred embodiment, the proteins of the present invention include a between about 10 and about 25 contiguous amino acid region, more preferably between about 20 and about 50 contiguous amino acid region and even more preferably a between about 40 and about 80 contiguous amino acid region. In a preferred embodiment the protein is selected from the group consisting of a plant, more preferably a maize or soybean (a) ketoacyl-thiolase or fragment thereof, a plant, more preferably a soybean or maize acyl-CoA oxidase.

In another preferred embodiment, the protein comprises an amino acid sequence selected from the group consisting of SEQ ID: 2, SEQ ID: 4, SEQ ID: 6, SEQ ID: 8, and SEQ ID: 10.

A protein of the invention can also be a homologue protein. A homologue can also be generated by molecular evolution or DNA shuffling techniques, so that the molecule retains at least one functional or structure characteristic of the original (see, for example, U.S. Pat. No. 5,811,238).

Protein molecules of the present invention include homologues of proteins or fragments thereof comprising a protein sequence selected from SEQ ID: 2, SEQ ID: 4, SEQ ID: 6, SEQ ID: 8, and SEQ ID: 10, or fragment thereof or encoded by SEQ ID: 1, SEQ ID: 3, SEQ ID: 5, SEQ ID: 7, and SEQ ID: 9 or fragments thereof. Preferred protein molecules of the invention include homologues of proteins or fragments having an amino acid sequence selected from the group consisting of SEQ ID: 2, SEQ ID: 4, SEQ ID: 6, SEQ ID: 8, and SEQ ID: 10 or fragment thereof. A homologue protein may be derived from, but not limited to, alfalfa, Arabidopsis, barley, Brassica, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm, maize, soybean Phaseolus etc. Particularly preferred species for use in the isolation of homologs would include, Arabidopsis, barley, cotton, oat, oilseed rape, rice, canola, ornamentals, sugarcane, sugarbeet, tomato, potato, wheat and turf grasses. Such a homologue can be obtained by any of a variety of methods. Most preferably, as indicated above, one or more of the disclosed sequences (such as SEQ ID: 1, SEQ ID: 3, SEQ ID: 5, SEQ ID: 7, and SEQ ID: 9 or complements thereof) will be used in defining a pair of primers to isolate the homologue-encoding nucleic acid molecules from any desired species. Such molecules can be expressed to yield protein homologues by recombinant means.

(c) Plant Constructs and Plant Transformants

One or more of the nucleic acid molecules of the invention may be used in plant transformation or transfection. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism. In a preferred embodiment the exogenous genetic material includes a nucleic acid molecule of the present invention, preferably a nucleic acid molecule having a sequence selected from the group consisting of SEQ ID: 1, SEQ ID: 3, SEQ ID: 5, SEQ ID: 7, and SEQ ID: 9 or complements thereof or fragments of either. Another preferred class of exogenous genetic material are nucleic acid molecules that encode a protein or fragment thereof having an amino acid selected from the group consisting of SEQ ID: 2, SEQ ID: 4, SEQ ID: 6, SEQ ID: 8, and SEQ ID: 10 or fragments thereof.

Such genetic material may be transferred into either monocotyledons and dicotyledons including, but not limited to maize, soybean, Arabidopsis, phaseolus, peanut, alfalfa, wheat, rice, oat, sorghum, rye, tritordeum, millet, fescue, perennial ryegrass, sugarcane, cranberry, papaya, banana, banana, muskmelon, apple, cucumber, dendrobium, gladiolus, chrysanthemum, liliacea, cotton, eucalyptus, sunflower, canola, turfgrass, sugarbeet, coffee and dioscorea (Christou, In: *Particle Bombardment for Genetic Engineering of Plants,* Biotechnology Intelligence Unit. Academic Press, San Diego, Calif. (1996)).

Transfer of a nucleic acid that encodes for a protein can result in overexpression of that protein in a transformed cell or transgenic plant. One or more of the proteins or fragments thereof encoded by nucleic acid molecules of the invention may be overexpressed in a transformed cell or transformed plant. Such overexpression may be the result of transient or stable transfer of the exogenous genetic material.

Exogenous genetic material may be transferred into a host cell by the use of a DNA vector or construct designed for such a purpose. Design of such a vector is generally within the skill of the art (See, *Plant Molecular Biology: A Laboratory Manual,* Clark (ed.), Springier, N.Y. (1997)).

A construct or vector may include a plant promoter to express the protein or protein fragment of choice. A number of promoters, which are active in plant cells, have been described in the literature. These include the nopaline synthase (NOS) promoter (Ebert et al., *Proc. Natl. Acad. Sci. (U.S.A.)* 84:5745–5749 (1987)), the octopine synthase (OCS) promoter (which are carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315–324 (1987)) and the CaMV 35S promoter (Odell et al., *Nature* 313:810–812 (1985)), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci. (U.S.A.)* 84:6624–6628 (1987)), the sucrose synthase promoter (Yang et al., *Proc. Natl. Acad. Sci. (U.S.A.)* 87:4144–4148 (1990)), the R gene complex promoter (Chandler et al., *The Plant Cell* 1:1175–1183 (1989)) and the chlorophyll a/b binding protein gene promoter, etc. These promoters have been used to create DNA constructs that have been expressed in plants; see, e.g., PCT publication WO 84/02913. The CaMV 35S promoters are preferred for use in plants. Promoters known or found to cause transcription of DNA in plant cells can be used in the invention.

For the purpose of expression in source tissues of the plant, such as the leaf, seed, root or stem, it is preferred that the promoters utilized have relatively high expression in these specific tissues. Tissue-specific expression of a protein of the present invention is a particularly preferred embodiment. For this purpose, one may choose from a number of promoters for genes with tissue- or cell-specific or -enhanced expression. Examples of such promoters reported in the literature include the chloroplast glutamine synthetase GS2 promoter from pea (Edwards et al., *Proc. Natl. Acad. Sci.* (*U.S.A.*) 87:3459–3463 (1990)), the chloroplast fructose-1,6-biphosphatase (FBPase) promoter from wheat (Lloyd et al., *Mol. Gen. Genet.* 225:209–216 (1991)), the nuclear photosynthetic ST-LS1 promoter from potato (Stockhaus et al., *EMBO J.* 8:2445–2451 (1989)), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773–778 (1994)), the promoter for the Cab-1 gene from wheat (Fejes et al., *Plant Mol. Biol.* 15:921–932 (1990)), the promoter for the CAB-1 gene from spinach (Lubberstedt et al., *Plant Physiol.* 104:997–1006 (1994)), the promoter for the cab1R gene from rice (Luan et al., *Plant Cell.* 4:971–981 (1992)), the pyruvate, orthophosphate dikinase (PPDK) promoter from maize (Matsuoka et al., *Proc. Natl. Acad. Sci.* (*U.S.A.*) 90: 9586–9590 (1993)), the promoter for the tobacco Lhcb1*2 gene (Cerdan et al., *Plant Mol. Biol.* 33:245–255 (1997)), the *Arabidopsis thaliana* SUC2 sucrose-H+ symporter promoter (Truernit et al., *Planta.* 196:564–570 (1995)) and the promoter for the thylakoid membrane proteins from spinach (psaD, psaF, psaE, PC, FNR, atpC, atpD, cab, rbcS). Other promoters for the chlorophyll a/b-binding proteins may also be utilized in the invention, such as the promoters for LhcB gene and PsbP gene from white mustard (*Sinapis alba;* Kretsch et al., *Plant Mol. Biol.* 28:219–229 (1995)).

For the purpose of expression in sink tissues of the plant, such as the tuber of the potato plant, the fruit of tomato, or the seed of maize, wheat, rice and barley, it is preferred that the promoters utilized in the invention have relatively high expression in these specific tissues. A number of promoters for genes with tuber-specific or -enhanced expression are known, including the class I patatin promoter (Bevan et al., *EMBO J.* 8:1899–1906 (1986); Jefferson et al., *Plant Mol. Biol.* 14:995–1006 (1990)), the promoter for the potato tuber ADPGPP genes, both the large and small subunits, the sucrose synthase promoter (Salanoubat and Belliard, *Gene* 60:47–56 (1987), Salanoubat and Belliard, *Gene* 84:181–185 (1989)), the promoter for the major tuber proteins including the 22 kd protein complexes and proteinase inhibitors (Hannapel, *Plant Physiol.* 101:703–704 (1993)), the promoter for the granule bound starch synthase gene (GBSS) (Visser et al., *Plant Mol. Biol.* 17:691–699 (1991)) and other class I and II patatins promoters (Koster-Topfer et al., *Mol Gen Genet.* 219:390–396 (1989); Mignery et al., *Gene.* 62:27–44 (1988)).

Other promoters can also be used to express a protein or fragment thereof in specific tissues, such as seeds or fruits. The promoter for β-conglycinin (Chen et al., *Dev. Genet.* 10: 112–122 (1989)) or other seed-specific promoters such as the napin and phaseolin promoters, can be used. The zeins are a group of storage proteins found in maize endosperm. Genomic clones for zein genes have been isolated (Pedersen et al., *Cell* 29:1015–1026 (1982)) and the promoters from these clones, including the 15 kD, 16 kD, 19 kD, 22 kD, 27 kD and genes, could also be used. Other promoters known to function, for example, in maize include the promoters for the following genes: waxy, Brittle, Shrunken 2, Branching enzymes I and II, starch synthases, debranching enzymes, oleosins, glutelins and sucrose synthases. A particularly preferred promoter for maize endosperm expression is the promoter for the glutelin gene from rice, more particularly the Osgt-1 promoter (Zheng et al., *Mol. Cell Biol.* 13:5829–5842 (1993)). Examples of promoters suitable for expression in wheat include those promoters for the ADP-glucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins.

Root specific promoters may also be used. An example of such a promoter is the promoter for the acid chitinase gene (Samac et al., *Plant Mol. Biol.* 25:587–596 (1994)). Expression in root tissue could also be accomplished by utilizing the root specific subdomains of the CaMV35S promoter that have been identified (Lam et al., *Proc. Natl. Acad. Sci.* (*U.S.A.*) 86:7890–7894 (1989)). Other root cell specific promoters include those reported by Conkling et al. (Conkling et al., *Plant Physiol.* 93:1203–1211 (1990)).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436. In addition, a tissue specific enhancer may be used (Fromm et al., *The Plant Cell* 1:977–984 (1989)).

Constructs or vectors may also include, with the coding region of interest, a nucleic acid sequence that acts, in whole or in part, to terminate transcription of that region. A number of such sequences have been isolated, including the Tr7 3' sequence and the NOS 3' sequence (Ingelbrecht et al., *The Plant Cell* 1:671–680 (1989); Bevan et al., *Nucleic Acids Res.* 11:369–385 (1983)).

A vector or construct may also include regulatory elements. Examples of such include the Adh intron 1 (Callis et al., *Genes and Develop.* 1:1183–1200 (1987)), the sucrose synthase intron (Vasil et al., *Plant Physiol.* 91:1575–1579 (1989)) and the TMV omega element (Gallie et al., *The Plant Cell* 1:301–311 (1989)). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.* 199:183–188 (1985)), which codes for kanamycin resistance and can be selected for using kanamycin, G418, etc.; a bar gene which codes for bialaphos resistance; a mutant EPSP synthase gene (Hinchee et al., *Bio/Technology* 6:915–922 (1988)) which encodes glyphosate resistance; a nitrilase gene which confers resistance to bromoxynil (Stalker et al., *J. Biol. Chem.* 263:6310–6314 (1988)); a mutant acetolactate synthase gene (ALS) which confers imidazolinone or sulphonylurea resistance (European Patent Application 154,204 (Sep. 11, 1985)); and a methotrexate resistant DHFR gene (Thillet et al., *J. Biol. Chem.* 263:12500–12508 (1988)).

A vector or construct may also include a transit peptide. Incorporation of a suitable chloroplast transit peptide may also be employed (European Patent Application Publication Number 0218571). Translational enhancers may also be incorporated as part of the vector DNA. DNA constructs could contain one or more 5' non-translated leader sequences which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393–405 (1996).

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, *Plant Mol. Biol, Rep.* 5:387–405 (1987); Jefferson et al., *EMBO J.* 6:3901–3907 (1987)); an R-locus gene, which encodes a product that regulates the production of anthocyanin pigments (red color) in plant tissues (Dellaporta et al., *Stadler Symposium* 11:263–282 (1988)); a β-lactamase gene (Sutcliffe et al., *Proc. Natl. Acad. Sci.* (*U.S.A.*) 75:3737–3741 (1978)), a gene which encodes an enzyme for which various chromogenic substrates are known (e.g., PADAC, a chromogenic cephalosporin); a luciferase gene (Ow et al., *Science* 234:856–859 (1986)); a xylE gene (Zukowsky et al., *Proc. Natl. Acad. Sci.* (*U.S.A.*) 80:1101–1105 (1983)) which encodes a catechol dioxygenase that can convert chromogenic catechols; an α-amylase gene (Ikatu et al., *Bio/Technol.* 8:241–242 (1990)); a tyrosinase gene (Katz et al., *J. Gen. Microbiol.* 129:2703–2714 (1983)) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by Agrobacterium infection or direct delivery of nucleic acid molecules such as, for example, by PEG-mediated transformation, by electroporation or by acceleration of DNA coated particles, etc (Potrykus, *Ann. Rev. Plant Physiol. Plant Mol. Biol.* 42:205–225 (1991); Vasil, *Plant Mol. Biol.* 25:925–937 (1994)). For example, electroporation has been used to transform maize protoplasts (Fromm et al., *Nature* 312:791–793 (1986)).

Other vector systems suitable for introducing transforming DNA into a host plant cell include but are not limited to binary artificial chromosome (BIBAC) vectors (Hamilton et al., *Gene* 200:107–116 (1997)); and transfection with RNA viral vectors (Della-Cioppa et al., *Ann. N.Y. Acad. Sci.* (1996), 792 (Engineering Plants for Commercial Products and Applications), 57–61). Additional vector systems also include plant selectable YAC vectors such as those described in Mullen et al., *Molecular Breeding* 4:449–457 (1988)).

Technology for introduction of DNA into cells is well known to those of skill in the art. Four general methods for delivering a gene into cells have been described: (1) chemical methods (Graham and van der Eb, *Virology* 54:536–539 (1973)); (2) physical methods such as microinjection (Capecchi, *Cell* 22:479–488 (1980)), electroporation (Wong and Neumann, *Biochem. Biophys. Res. Commun.* 107:584–587 (1982); Fromm et al., *Proc. Natl. Acad. Sci.* (*U.S.A.*) 82:5824–5828 (1985); U.S. Pat. No. 5,384,253); and the gene gun (Johnston and Tang, *Methods Cell Biol.* 43:353–365 (1994)); (3) viral vectors (Clapp, *Clin. Perinatol.* 20:155–168 (1993); Lu et al., *J. Exp. Med.* 178:2089–2096 (1993); Eglitis and Anderson, *Biotechniques* 6:608–614 (1988)); and (4) receptor-mediated mechanisms (Curiel et al., *Hum. Gen. Ther.* 3:147–154 (1992), Wagner et al., *Proc. Natl. Acad. Sci.* (*USA*) 89:6099–6103 (1992)).

Acceleration methods that may be used include, for example, microprojectile bombardment and the like. One example of a method for delivering transforming nucleic acid molecules to plant cells is microprojectile bombardment. This method has been reviewed by Yang and Christou (eds.), *Particle Bombardment Technology for Gene Transfer,* Oxford Press, Oxford, England (1994)). Non-biological particles (microprojectiles) that may be coated with nucleic acids and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol.* 87:671–674 (1988)) nor the susceptibility of Agrobacterium infection are required. An illustrative embodiment of a method for delivering DNA into maize cells by acceleration is a biolistics α-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell* 2:603–618 (1990)). The screen disperses the tungsten nucleic acid particles so that they are not delivered to the recipient cells in large aggregates. A particle delivery system suitable for use with the invention is the helium acceleration PDS-1000/He gun is available from Bio-Rad Laboratories (Bio-Rad, Hercules, Calif.)(Sanford et al., *Technique* 3:3–16 (1991)).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci. (U.S.A.)* 87:8526–8530 (1990); Svab and Maliga, *Proc. Natl. Acad. Sci. (U.S.A.)* 90:913–917 (1993); Staub and Maliga, *EMBO J.* 12:601–606 (1993); U.S. Pat. Nos. 5,451,513 and 5,545,818).

Accordingly, it is contemplated that one may wish to adjust various aspects of the bombardment parameters in small scale studies to fully optimize the conditions. One may particularly wish to adjust physical parameters such as gap distance, flight distance, tissue distance and helium pressure. One may also minimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example the methods described by Fraley et al., *Bio/Technology* 3:629–635 (1985) and Rogers et al., *Methods Enzymol.* 153:253–277 (1987). Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.* 205:34 (1986)).

Modern Agrobacterium transformation vectors are capable of replication in *E. coli* as well as Agrobacterium, allowing for convenient manipulations as described (Klee et al., In: *Plant DNA Infectious Agents,* Hohn and Schell (eds.), Springer-Verlag, New York, pp. 179–203 (1985)). Moreover, technological advances in vectors for Agrobacterium-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Methods Enzymol.* 153:253–277 (1987)). In addition, Agrobacterium containing both armed and disarmed Ti genes can be used for the transformations. In those plant strains where Agrobacterium-mediated transformation is efficient, it is the method of choice because of the facile and defined nature of the gene transfer.

A transgenic plant formed using Agrobacterium transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for the gene of interest.

It is also to be understood that two different transgenic plants can also be mated to produce offspring that contain two independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (See, for example, Potrykus et al., *Mol. Gen. Genet.* 205:193–200 (1986); Lorz et al., *Mol. Gen. Genet.* 199:178 (1985); Fromm et al., *Nature* 319:791 (1986); Uchimiya et al., *Mol. Gen. Genet.* 204:204 (1986); Marcotte et al., *Nature* 335:454–457 (1988)).

Application of these systems to different plant strains depends upon the ability to regenerate that particular plant strain from protoplasts. Illustrative methods for the regeneration of cereals from protoplasts are described (Fujimura et al., *Plant Tissue Culture Letters* 2:74 (1985); Toriyama et al., *Theor Appl. Genet.* 205:34 (1986); Yamada et al., *Plant Cell Rep.* 4:85 (1986); Abdullah et al., *Biotechnology* 4:1087 (1986)).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology* 6:397 (1988)). In addition, "particle gun" or high-velocity microprojectile technology can be utilized (Vasil et al., *Bio/Technology* 10:667 (1992)).

Using the latter technology, DNA is carried through the cell wall and into the cytoplasm on the surface of small metal particles as described (Klein et al., *Nature* 328:70 (1987); Klein et al., *Proc. Natl. Acad. Sci. (U.S.A.)*

85:8502–8505 (1988); McCabe et al., *Bio/Technology* 6:923 (1988)). The metal particles penetrate through several layers of cells and thus allow the transformation of cells within tissue explants.

Other methods of cell transformation can also be used and include but are not limited to introduction of DNA into plants by direct DNA transfer into pollen (Hess et al., *Intern Rev. Cytol.* 107:367 (1987); Luo et al., *Plant Mol Biol. Reporter* 6:165 (1988)), by direct injection of DNA into reproductive organs of a plant (Pena et al., *Nature* 325:274 (1987)), or by direct injection of DNA into the cells of immature embryos followed by the rehydration of desiccated embryos (Neuhaus et al., *Theor. Appl. Genet.* 75:30 (1987)).

The regeneration, development and cultivation of plants from single plant protoplast transformants or from various transformed explants is well known in the art (Weissbach and Weissbach, In: *Methods for Plant Molecular Biology*, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. Nos. 5,004,863; 5,159,135; 5,518,908); soybean (U.S. Pat. Nos. 5,569,834; 5,416,011; McCabe et. al., *Biotechnology* 6:923 (1988); Christou et al., *Plant Physiol.* 87:671–674 (1988)); Brassica (U.S. Pat. No. 5,463,174); peanut (Cheng et al., *Plant Cell Rep.* 15:653–657 (1996), McKently et al., *Plant Cell Rep.* 14:699–703 (1995)); papaya; and pea (Grant et al., *Plant Cell Rep.* 15:254–258 (1995)).

Transformation of monocotyledons using electroporation, particle bombardment and Agrobacterium have also been reported. Transformation and plant regeneration have been achieved in asparagus (Bytebier et al., *Proc. Natl. Acad. Sci. (USA)* 84:5354 (1987)); barley (Wan and Lemaux, *Plant Physiol* 104:37 (1994)); maize (Rhodes et al., *Science* 240:204 (1988); Gordon-Kamm et al., *Plant Cell* 2:603–618 (1990); Fromm et al., *Bio/Technology* 8:833 (1990); Koziel et al., *Bio/Technology* 11:194 (1993); Armstrong et al., *Crop Science* 35:550–557 (1995)); oat (Somers et al., *Bio/Technology* 10:1589 (1992)); orchard grass (Horn et al., *Plant Cell Rep.* 7:469 (1988)); rice (Toriyama et al., *Theor Appl. Genet.* 205:34 (1986); Part et al., *Plant Mol. Biol.* 32:1135–1148 (1996); Abedinia et al., *Aust. J. Plant Physiol.* 24:133–141 (1997); Zhang and Wu, *Theor. Appl. Genet.* 76:835 (1988); Zhang et al., *Plant Cell Rep.* 7:379 (1988); Battraw and Hall, *Plant Sci.* 86:191–202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)) and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454–457 (1988); Marcotte et al., *Plant Cell* 1:523–532 (1989); McCarty et al., *Cell* 66:895–905 (1991); Hattori et al., *Genes Dev.* 6:609–618 (1992); Goff et al., *EMBO J.* 9:2517–2522 (1990)). Transient expression systems may be used to functionally dissect gene constructs (see generally, Mailga et al., *Methods in Plant Molecular Biology*, Cold Spring Harbor Press (1995)).

Any of the nucleic acid molecules of the invention may be introduced into a plant cell in a permanent or transient manner in combination with other genetic elements such as vectors, promoters, enhancers, etc. Further, any of the nucleic acid molecules of the invention may be introduced into a plant cell in a manner that allows for overexpression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279–289 (1990); van der Krol et al., *Plant Cell* 2:291–299 (1990)). Cosuppression may result from stable transformation with a single copy nucleic acid molecule that is homologous to a nucleic acid sequence found with the cell (Prolls and Meyer, *Plant J.* 2:465–475 (1992)) or with multiple copies of a nucleic acid molecule that is homologous to a nucleic acid sequence found with the cell (Mittlesten et al., *Mol. Gen. Genet.* 244:325–330 (1994)). Genes, even though different, linked to homologous promoters may result in the cosuppression of the linked genes (Vaucheret, *C.R. Acad. Sci. III* 316:1471–1483 (1993); Flavell, *Proc. Natl. Acad. Sci. (U.S.A.)* 91:3490–3496 (1994)); van Blokland et al., *Plant J.* 6:861–877 (1994); Jorgensen, *Trends Biotechnol.* 8:340–344 (1990); Meins and Kunz, In: *Gene Inactivation and Homologous Recombination in Plants*, Paszkowski (ed.), pp. 335–348, Kluwer Academic, Netherlands (1994)).

It is understood that one or more of the nucleic acids of the invention may be introduced into a plant cell and transcribed using an appropriate promoter with such transcription resulting in the cosuppression of an endogenous protein.

Antisense approaches are a way of preventing or reducing gene function by targeting the genetic material (Mol et al., *FEBS Lett.* 268:427–430 (1990)). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.), Vol. 11, New York: Plenum 49–63 (1989)).

The principle of regulation by antisense RNA is that RNA that is complementary to the target mRNA is introduced into cells, resulting in specific RNA:RNA duplexes being formed by base pairing between the antisense substrate and the target mRNA (Green et al., *Annu. Rev. Biochem.* 55:569–597 (1986)). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155–184 (1990)). An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

It is understood that the activity of a protein in a plant cell may be reduced or depressed by growing a transformed plant cell containing a nucleic acid molecule whose non-transcribed strand encodes a protein or fragment thereof.

Posttranscriptional gene silencing (PTGS) can result in virus immunity or gene silencing in plants. PTGS is induced by dsRNA and is mediated by an RNA-dependent RNA polymerase, present in the cytoplasm, that requires a dsRNA template. The dsRNA is formed by hybridization of complementary transgene mRNAs or complementary regions of the same transcript. Duplex formation can be accomplished by using transcripts from one sense gene and one antisense gene colocated in the plant genome, a single transcript that has self-complementarity, or sense and antisense transcripts from genes brought together by crossing. The dsRNA-dependent RNA polymerase makes a complementary strand from the transgene mRNA and RNAse molecules attach to this complementary strand (cRNA). These cRNA-RNAse molecules hybridize to the endogene mRNA and cleave the single-stranded RNA adjacent to the hybrid. The cleaved single-stranded RNAs are further degraded by other host RNAses because one will lack a capped 5' end and the other will lack a poly(A) tail (Waterhouse et al., *PNAS* 95: 13959–13964 (1998)).

It is understood that one or more of the nucleic acids of the invention may be introduced into a plant cell and transcribed using an appropriate promoter with such transcription resulting in the postranscriptional gene silencing of an endogenous transcript.

Antibodies have been expressed in plants (Hiatt et al., *Nature* 342:76–78 (1989); Conrad and Fielder, *Plant Mol. Biol.* 26:1023–1030 (1994)). Cytoplasmic expression of a scFv (single-chain Fv antibodies) has been reported to delay infection by artichoke mottled crinkle virus. Transgenic plants that express antibodies directed against endogenous proteins may exhibit a physiological effect (Philips et al., *EMBO J.* 16:4489–4496 (1997); Marion-Poll, *Trends in Plant Science* 2:447–448 (1997)). For example, expressed anti-abscissic antibodies have been reported to result in a general perturbation of seed development (Philips et al., *EMBO J.* 16: 4489–4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15:1313–1315 (1997); Baca et al., *Ann. Rev. Biophys. Biomol. Struct.* 26:461–493 (1997)). The catalytic abilities of abzymes may be enhanced by site directed mutagenesis. Examples of abzymes are, for example, set forth in U.S. Pat. Nos. 5,658,753; 5,632,990; 5,631,137; 5,602,015; 5,559,538; 5,576,174; 5,500,358; 5,318,897; 5,298,409; 5,258,289 and 5,194,585.

It is understood that any of the antibodies of the invention may be expressed in plants and that such expression can result in a physiological effect. It is also understood that any of the expressed antibodies may be catalytic.

The present invention also provides for parts of the plants of the present invention. Plant parts, without limitation, include seed, endosperm, ovule and pollen. In a particularly preferred embodiment of the present invention, the plant part is a seed.

Exemplary Uses

Nucleic acid molecules and fragments thereof of the invention may be employed to obtain other nucleic acid molecules from the same species (nucleic acid molecules from maize may be utilized to obtain other nucleic acid molecules from maize). Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries. Methods for forming such libraries are well known in the art.

Nucleic acid molecules and fragments thereof of the invention may also be employed to obtain nucleic acid homologues. Such homologues include the nucleic acid molecule of other plants or other organisms (e.g., alfalfa, Arabidopsis, barley, Brassica, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm, Phaseolus, etc.) including the nucleic acid molecules that encode, in whole or in part, protein homologues of other plant species or other organisms, sequences of genetic elements, such as promoters and transcriptional regulatory elements. Such molecules can be readily obtained by using the above-described nucleic acid molecules or fragments thereof to screen cDNA or genomic libraries obtained from such plant species. Methods for forming such libraries are well known in the art. Such homologue molecules may differ in their nucleotide sequences from those found in one or more of SEQ ID: 1, SEQ ID: 3, SEQ ID: 5, SEQ ID: 7, and SEQ ID: 9 or complements thereof because complete complementarity is not needed for stable hybridization. The nucleic acid molecules of the invention therefore also include molecules that, although capable of specifically hybridizing with the nucleic acid molecules may lack "complete complementarity."

Any of a variety of methods may be used to obtain one or more of the above-described nucleic acid molecules (Zamechik et al., *Proc. Natl. Acad. Sci.* (*U.S.A.*) 83:4143–4146 (1986); Goodchild et al., *Proc. Natl. Acad. Sci.* (*U.S.A.*) 85:5507–5511 (1988); Wickstrom et al., *Proc. Natl. Acad. Sci.* (*U.S.A.*) 85:1028–1032 (1988); Holt et al., *Molec. Cell. Biol.* 8:963–973 (1988); Gerwirtz et al., *Science* 242:1303–1306 (1988); Anfossi et al., *Proc. Natl. Acad. Sci.*

(U.S.A.) 86:3379–3383 (1989); Becker et al., *EMBO J.* 8:3685–3691 (1989)). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263–273 (1986); Erlich et al., European Patent 50,424; European Patent 84,796; European Patent 258,017; European Patent 237,362; Mullis, European Patent 201,184; Mullis et al., U.S. Pat. No. 4,683,202; Erlich, U.S. Pat. No. 4,582,788; and Saiki et al., U.S. Pat. No. 4,683,194) to amplify and obtain any desired nucleic acid molecule or fragment.

Promoter sequences and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating nucleic acid molecules of the present invention with members of genomic libraries and recovering clones that hybridize to such nucleic acid molecules thereof. In a second embodiment, methods of "chromosome walking," or inverse PCR may be used to obtain such sequences (Frohman et al., *Proc. Natl. Acad. Sci. (U.S.A.)* 85:8998–9002 (1988); Ohara et al., *Proc. Natl. Acad. Sci. (U.S.A.)* 86:5673–5677 (1989); Pang et al., *Biotechniques* 22:1046–1048 (1977); Huang et al., *Methods Mol. Biol.* 69:89–96 (1997); Huang et al., *Method Mol. Biol.* 67:287–294 (1997); Benkel et al., *Genet. Anal.* 13:123–127 (1996); Hartl et al., *Methods Mol. Biol.* 58:293–301 (1996)). The term "chromosome walking" means a process of extending a genetic map by successive hybridization steps.

The nucleic acid molecules of the invention may be used to isolate promoters of cell enhanced, cell specific, tissue enhanced, tissue specific, developmentally or environmentally regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (See, for example, Birren et al., *Genome Analysis: Analyzing DNA*, 1, (1997), Cold Spring Harbor Laboratory Press, Cold Spring Harbor, N.Y.). Promoters obtained utilizing the nucleic acid molecules of the invention could also be modified to affect their control characteristics. Examples of such modifications would include but are not limited to enhancer sequences. Such genetic elements could be used to enhance gene expression of new and existing traits for crop improvement.

Another subset of the nucleic acid molecules of the invention includes nucleic acid molecules that are markers. The markers can be used in a number of conventional ways in the field of molecular genetics. Such markers include nucleic acid molecules SEQ ID: 1, SEQ ID: 3, SEQ ID: 5, SEQ ID: 7, and SEQ ID: 9 or complements thereof or fragments of either that can act as markers and other nucleic acid molecules of the present invention that can act as markers.

Genetic markers of the invention include "dominant" or "codominant" markers. "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is in either the homozygous or heterozygous condition. The absence of the dominant marker phenotype (e.g., absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

SNPs can be characterized using any of a variety of methods (Botstein et al., *Am. J. Hum. Genet.* 32:314–331 (1980); Konieczny and Ausubel, *Plant J.* 4:403–410 (1993); Myers et al., *Nature* 313:495–498 (1985); Newton et al., *Nucl. Acids Res.* 17:2503–2516 (1989); Wu et al., *Proc. Natl. Acad. Sci. (U.S.A.)* 86:2757–2760 (1989); Barany, *Proc. Natl. Acad. Sci. (U.S.A.)* 88:189–193 (1991); Labrune et al., *Am. J. Hum. Genet.* 48: 1115–1120 (1991); Kuppuswami et al., *Proc. Natl. Acad. Sci. USA* 88:1143–1147 (1991); Sarkar et al., *Genomics* 13:441–443 (1992); Nikiforov et al., *Nucl. Acids Res.* 22:4167–4175 (1994); Livak et al., *PCR Methods Appl.* 4:357–362 (1995); Livak et al., *Nature Genet.* 9:341–342 (1995); Chen and Kwok, *Nucl. Acids Res.* 25:347–353 (1997); Tyagi et al., *Nature Biotech.* 16: 49–53 (1998); Haff and Smirnov, *Genome Res.* 7: 378–388 (1997); Neff et al., *Plant J.* 14:387–392 (1998)).

Additional markers, such as AFLP markers, RFLP markers and RAPD markers, can be utilized (Walton, *Seed World* 22–29 (July, 1993); Burow and Blake, *Molecular Dissection of Complex Traits*, 13–29, Paterson (ed.), CRC Press, New York (1988)). Another marker type, RAPDs, are developed from DNA amplification with random primers and result from single base changes and insertions/deletions in plant genomes. They are dominant markers with a medium level of polymorphisms and are highly abundant. AFLP markers require using the PCR on a subset of restriction fragments from extended adapter primers. These markers are both dominant and codominant are highly abundant in genomes and exhibit a medium level of polymorphism.

The genomes of animals and plants naturally undergo spontaneous mutation in the course of their continuing evolution (Gusella, *Ann. Rev. Biochem.* 55:831–854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e., the original "allele") whereas other members may have the variant sequence (i.e., the variant "allele"). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides.

Polymorphisms characterized by such tandem repeats are referred to as "variable number tandem repeat" ("VNTR") polymorphisms. VNTRs have been used in identity analysis (Weber, U.S. Pat. No. 5,075,217; Armour et al., *FEBS Lett.* 307:113–115 (1992); Jones et al., *Eur. J. Haematol.* 39:144–147 (1987); Horn et al., PCT Patent Application WO91/14003; Jeffreys, European Patent Application 370, 719; Jeffreys, U.S. Pat. No. 5,175,082; Jeffreys et al., *Amer. J. Hum. Genet.* 39:11–24 (1986); Jeffreys et al., *Nature* 316:76–79 (1985); Gray et al., *Proc. R. Acad. Soc. Lond.* 243:241–253 (1991); Moore et al., *Genomics* 10:654–660 (1991); Jeffreys et al., *Anim. Genet.* 18:1–15 (1987); Hillel et al., *Anim. Genet.* 20:145–155 (1989); Hillel et al., *Genet.* 124:783–789 (1990)).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s) and more preferably within 100 kb of the polymorphism(s) and most preferably within 10 kb of the polymorphism(s) can be employed.

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms" ("RFLPs") (Glassberg, UK Patent Application 2135774; Skolnick et al., *Cytogen. Cell Genet.* 32:58–67 (1982); Botstein et al., *Ann. J. Hum. Genet.* 32:314–331 (1980); Fischer et al., (PCT Application WO90/13668; Uhlen, PCT Application WO90/11369).

Polymorphisms can also be identified by Single Strand Conformation Polymorphism (SSCP) analysis (Elles, *Methods in Molecular Medicine: Molecular Diagnosis of Genetic Diseases,* Humana Press (1996)); Orita et al., *Genomics* 5:874–879 (1989)). A number of protocols have been described for SSCP including, but not limited to, Lee et al., *Anal. Biochem.* 205:289–293 (1992); Suzuki et al., *Anal. Biochem.* 192:82–84 (1991); Lo et al., *Nucleic Acids Research* 20:1005–1009 (1992); Sarkar et al., *Genomics* 13:441–443 (1992). It is understood that one or more of the nucleic acids of the invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA (Vos et al., *Nucleic Acids Res.* 23:4407–4414 (1995)). This method allows for the specific co-amplification of high numbers of restriction fragments, which can be visualized by PCR without knowledge of the nucleic acid sequence. It is understood that one or more of the nucleic acids of the invention, may be utilized as markers or probes to detect polymorphisms by AFLP analysis or for fingerprinting RNA.

Polymorphisms may also be found using random amplified polymorphic DNA (RAPD) (Williams et al., *Nucl. Acids Res.* 18:6531–6535 (1990)) and cleaveable amplified polymorphic sequences (CAPS) (Lyamichev et al., *Science* 260:778–783 (1993)). It is understood that one or more of the nucleic acid molecules of the invention, may be utilized as markers or probes to detect polymorphisms by RAPD or CAPS analysis.

Through genetic mapping, a fine scale linkage map can be developed using DNA markers and, then, a genomic DNA library of large-sized fragments can be screened with molecular markers linked to the desired trait. Molecular markers are advantageous for agronomic traits that are otherwise difficult to tag, such as resistance to pathogens, insects and nematodes, tolerance to abiotic stress, quality parameters and quantitative traits such as high yield potential. Here, an altered phytosterol level are preferred traits.

Essential requirements for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botstein, *Genetics* 121:185–199 (1989) and the interval mapping, based on maximum likelihood methods described by Lander and Botstein, *Genetics* 121:185–199 (1989) and implemented in the software package MAPMAKER/QTL (Lincoln and Lander, *Mapping Genes Controlling Quantitative Traits Using MAPMAKER/QTL,* Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics* 121:185–199 (1989) and further described by Arús and Moreno-González, *Plant Breeding,* Hayward et al., (eds.) Chapman & Hall, London, pp. 314–331 (1993).

Additional models can be used. Many modifications and alternative approaches to interval mapping have been reported, including the use non-parametric methods (Kruglyak and Lander, *Genetics* 139:1421–1428 (1995)). Multiple regression methods or models can be also be used, in which the trait is regressed on a large number of markers (Jansen, *Biometrics in Plant Breeding,* van Oijen and Jansen (eds.), Proceedings of the Ninth Meeting of the Eucarpia Section Biometrics in Plant Breeding, The Netherlands, pp.

116–124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval and at the same time onto a number of markers that serve as 'cofactors,' have been reported by Jansen and Stam, *Genetics* 136:1447–1455 (1994), and Zeng, *Genetics* 136:1457–1468 (1994). Generally, the use of cofactors reduces the bias and sampling error of the estimated QTL positions (Utz and Melchinger, *Biometrics in Plant Breeding*, van Oijen and Jansen (eds.) Proceedings of the Ninth Meeting of the Eucarpia Section Biometrics in Plant Breeding, The Netherlands, pp.195–204 (1994), thereby improving the precision and efficiency of QTL mapping (Zeng, *Genetics* 136:1457–1468 (1994)). These models can be extended to multi-environment experiments to analyze genotype-environment interactions (Jansen et al., *Theo. Appl. Genet.* 91:33–37 (1995)).

It is understood that one or more of the nucleic acid molecules of the invention may be used as molecular markers. It is also understood that one or more of the protein molecules of the invention may be used as molecular markers.

In accordance with this aspect of the invention, a sample nucleic acid is obtained from plant cells or tissues. Any source of nucleic acid may be used. Preferably, the nucleic acid is genomic DNA. The nucleic acid is subjected to restriction endonuclease digestion. For example, one or more nucleic acid molecule or fragment thereof of the invention can be used as a probe in accordance with the above-described polymorphic methods. The polymorphism obtained in this approach can then be cloned to identify the mutation at the coding region, which alters structure, or regulatory region of the gene, which affects its expression level.

In an aspect of the present invention, one or more of the nucleic molecules of the present invention are used to determine the level (i.e., the concentration of mRNA in a sample, etc.) in a plant (preferably maize or soybean) or pattern (i.e., the kinetics of expression, rate of decomposition, stability profile, etc.) of the expression of a protein encoded in part or whole by one or more of the nucleic acid molecule of the present invention (collectively, the "Expression Response" of a cell or tissue).

As used herein, the Expression Response manifested by a cell or tissue is said to be "altered" if it differs from the Expression Response of cells or tissues of plants not exhibiting the phenotype. To determine whether a Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g. disease resistance, pest tolerance, environmental tolerance such as tolerance to abiotic stress, male sterility, quality improvement or yield etc.). A change in genotype or phenotype may be transient or permanent. Also as used herein, a tissue sample is any sample that comprises more than one cell. In a preferred aspect, a tissue sample comprises cells that share a common characteristic (e.g. derived from root, seed, flower, leaf, stem or pollen etc.).

In one aspect of the present invention, an evaluation can be conducted to determine whether a particular mRNA molecule is present. One or more of the nucleic acid molecules of the present invention, preferably one or more of the nucleic acid molecules of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A number of methods can be used to compare the expression response between two or more samples of cells or tissue. These methods include hybridization assays, such as Northerns, RNAse protection assays, and in situ hybridization. Alternatively, the methods include PCR-type assays. In a preferred method, the expression response is compared by hybridizing nucleic acids from the two or more samples to an array of nucleic acids. The array contains a plurality of suspected sequences known or suspected of being present in the cells or tissue of the samples.

An advantage of in situ hybridization over more conventional techniques for the detection of nucleic acids is that it allows an investigator to determine the precise spatial population (Angerer et al., *Dev. Biol.* 101:477–484 (1984); Angerer et al., *Dev. Biol.* 112:157–166 (1985); Dixon et al., *EMBO J.* 10:1317–1324 (1991)). In situ hybridization may be used to measure the steady-state level of RNA accumulation (Hardin et al., *J. Mol. Biol.* 202:417–431 (1989)). A number of protocols have been devised for in situ hybridization, each with tissue preparation, hybridization and washing conditions (Meyerowitz, *Plant Mol. Biol. Rep.* 5:242–250 (1987); Cox and Goldberg, In: *Plant Molecular Biology: A Practical Approach,* Shaw (ed.), pp. 1–35, IRL Press, Oxford (1988); Raikhel et al., *In situ RNA hybridization in plant tissues,* In: *Plant Molecular Biology Manual,* vol. B9:1–32, Kluwer Academic Publisher, Dordrecht, Belgium (1989)).

In situ hybridization also allows for the localization of proteins within a tissue or cell (Wilkinson, *In Situ Hybridization,* Oxford University Press, Oxford (1992); Langdale, *In Situ Hybridization* In: *The Maize Handbook,* Freeling and Walbot (eds.), pp. 165–179, Springer-Verlag, New York (1994)). It is understood that one or more of the molecules of the invention, preferably one or more of the nucleic acid molecules or fragments thereof of the invention or one or more of the antibodies of the invention may be utilized to detect the level or pattern of a protein or mRNA thereof by in situ hybridization.

Fluorescent in situ hybridization allows the localization of a particular DNA sequence along a chromosome which is useful, among other uses, for gene mapping, following chromosomes in hybrid lines or detecting chromosomes with translocations, transversions or deletions. In situ hybridization has been used to identify chromosomes in several plant species (Griffor et al., *Plant Mol. Biol.* 1 7:101–109 (1991); Gustafson et al., *Proc. Natl. Acad. Sci. (U.S.A.)* 87:1899–1902 (1990); Mukai and Gill, *Genome* 34:448–452 (1991); Schwarzacher and Heslop-Harrison, Genome 34:317–323 (1991); Wang et al., *Jpn. J. Genet.* 66:313–316 (1991); Parra and Windle, *Nature Genetics* 5:17–21 (1993)). It is understood that the nucleic acid molecules of the invention may be used as probes or markers to localize sequences along a chromosome.

Another method to localize the expression of a molecule is tissue printing. Tissue printing provides a way to screen, at the same time on the same membrane many tissue sections from different plants or different developmental stages (Yomo and Taylor, *Planta* 112:35–43 (1973); Harris and Chrispeels, *Plant Physiol.* 56:292–299 (1975); Cassab and Varner, *J. Cell. Biol.* 105:2581–2588 (1987); Spruce et al., *Phytochemistry* 26:2901–2903 (1987); Barres et al., *Neuron* 5:527–544 (1990); Reid and Pont-Lezica, *Tissue Printing: Tools for the Study of Anatomy, Histochemistry and Gene Expression,* Academic Press, New York, N.Y. (1992); Reid et al., *Plant Physiol.* 93:160–165 (1990); Ye et al., *Plant J.* 1:175–183 (1991)).

It is understood that one or more of the molecules of the invention, preferably one or more of the nucleic acid molecules of the present invention or one or more of the antibodies of the invention may be utilized to detect the presence or quantity of a protein or fragment of the invention by tissue printing.

Further it is also understood that any of the nucleic acid molecules of the invention may be used as marker nucleic acids and or probes in connection with methods that require probes or marker nucleic acids. As used herein, a probe is an agent that is utilized to determine an attribute or feature (e.g. presence or absence, location, correlation, etc.) of a molecule, cell, tissue or plant. As used herein, a marker nucleic acid is a nucleic acid molecule that is utilized to determine an attribute or feature (e.g., presence or absence, location, correlation, etc.) or a molecule, cell, tissue or plant.

A microarray-based method for high-throughput monitoring of gene expression may be utilized to measure expression response. Schena et al., *Science* 270:467–470 (1995); cmgm.stanford.edu/pbrown/array.html; Shalon, Ph.D. Thesis, Stanford University (1996). This approach is based on using arrays of DNA targets (e.g. cDNA insets, colonies, or polymerase chain reaction products) for hybridization to a "complex probe" prepared with RNA extracted from a given cell line or tissue. The probe may be produced by reverse transcription of mRNA or total RNA and labeled with radioactive or fluorescent labeling. The probe is complex in that in contains many different sequences in various amounts, corresponding to the numbers of copies of the original mRNA species extracted from the sample.

The initial RNA source will typically be derived from a physiological source. The physiological source may be derived from a variety of eukaryotic sources, with physiological sources of interest including sources derived from single celled organisms such as yeast and multicellular organisms, including plants and animals, particularly plants, where the physiological sources from multicellular organisms may be derived from particular organs or tissues of the multicellular organism, or from isolated cells derived therefrom. The physiological sources may be derived from multicellular organisms at different developmental stages (e.g. 10 day old seedlings), grown under different environmental conditions (e.g., drought stressed plants) or treated with chemicals.

In obtaining the sample of RNAs to be analyzed from the physiological source from which it is derived, the physiological source may be subjected to a number of different processing steps, where such processing steps might include tissue homogenation, cell isolation and cytoplasmic extraction, nucleic acid extraction and the like, where such processing steps are known to the those of skill in the art. Methods of isolating RNA from cells, tissues, organs or whole organisms are known to those of skill in the art and are described in Maniatis et al., Molecular Cloning: A Laboratory Manual (Cold Spring Harbor Press) (1989).

The DNA may be placed on nylon or glass "microarrays" regularly arranged with a spot spacing of 1 mm or less. Expression levels can be measured for hundreds or thousands of genes, by using less than 2 micrograms of polyA+ RNA and determining the relative mRNA abundances down to one in ten thousand or less (Granjeaud et. al., *BioEssays* 21:781–790 (1999)).

In addition to arrays of cDNA clones or inserts, arrays of oligonucleotides are also used to study differential gene expression. In an oligonucleotide array, the genes of interest are represented by a series of 20 nucleotide oligomers that are unique to each gene. Labeled mRNA is prepared and hybridization signals are detected from specific sets of oligos that represent different genes supplemented by a set of control oligonucleotides. Potential advantages of the oligonucleotide array include enhanced specificity and sensitivity through the parallel analysis of "perfect match" oligos and "mismatch" oligos for each gene. The hybridization conditions can be adjusted to distinguish a perfect heteroduplex from a single base mismatch, thus allowing subtraction of nonspecific hybridization signals from specific hybridization signals. A disadvantage of oligonucleotide arrays relative to cDNA arrays is the limitation of the technology to genes of known sequence (Granjeaud et. al., *BioEssays* 21:781–790 (1991); Carulli et al., *Journal of Cellular Biochemistry Supplements* 30/31:286–296 (1998)).

These techniques have been successfully used to characterize patterns of gene expression associated with, for example, various important physiological changes in yeast, including the mitotic cell cycle, the heat shock response, and comparison between mating types. Once a set of comparable expression profiles is obtained, e.g. for cells at different time points or at different cellular states, a clustering algorithm generally is used to group sets of genes which share similar expression patterns. The clusters obtained can then be analyzed in the light of available functional annotations, often leading to associations of poorly characterized genes with genes whose function and regulation are better understood.

Regulatory networks that control gene expression can be characterized using microarray technology (DeRisi et al., *Science* 278: 680–686 (1997); Winzler et al. *Science* 28: 1194–1197 (1998); Cho et al. *Mol Cell* 2: 65–73 (1998); Spellman et al. *Mol Biol Cell* 95: 14863–14868 (1998). For example, it is has been reported that both cDNA and oligonucleotide arrays have been used to monitor gene expression in synchronized cell cultures. Analysis of the corresponding temporal patterns of gene expression resulted in the identification of over 400 cell cycle-regulated genes. In order to identify possible common regulatory mechanisms accounting for co-expression, consensus motifs in putative regulatory sequences upstream of the corresponding ORFs were examined. This resulted in the identification of several new potential binding sites for known factors or complexes involved in the coordinated transcription of genes during specific phases of the cell cycle (Thieffry, D. *BioEssays* 21: 895–899 (1999)).

The microarray approach may be used with polypeptide targets (U.S. Pat. Nos. 5,445,934; 5,143,854; 5,079,600; 4,923,901) synthesized on a substrate (microarray) and these polypeptides can be screened with either (Fodor et al., *Science* 251:767–773 (1991)). It is understood that one or more of the nucleic acid molecules or protein or fragments thereof of the invention may be utilized in a microarray-based method.

In another even more preferred embodiment of the present invention microarrays may be prepared that comprise nucleic acid molecules where such nucleic acid molecules include at least one, preferably at least two, more preferably at least three or more nucleic acid molecules or fragments thereof comprising a nucleic acid molecule selected from the group consisting of SEQ ID: 1, SEQ ID: 3, SEQ ID: 5, SEQ ID: 7, and SEQ ID: 9.

In another even more preferred embodiment of the present invention microarrays may be prepared that comprise nucleic acid molecules where such nucleic acid molecules include at least one, preferably at least two, more preferably at least three or more nucleic acid molecules or fragments thereof which specifically hybridize to one or more nucleic acid molecules selected from the group consisting of SEQ ID: 1, SEQ ID: 3, SEQ ID: 5, SEQ ID: 7, and SEQ ID: 9.

In yet another even more preferred embodiment of the present invention microarrays may be prepared that comprise nucleic acid molecules where such nucleic acid molecules encode at least one, preferably at least two, more preferably at least three or more proteins or fragment thereof comprising an amino acid sequence selected from the group consisting of a maize or soybean ketoacyl-thiolase or fragment thereof or maize or soybean acyl-CoA oxidase or fragment thereof.

Site directed mutagenesis may be utilized to modify nucleic acid sequences, particularly as it is a technique that allows one or more of the amino acids encoded by a nucleic acid molecule to be altered (e.g., a threonine to be replaced by a methionine) (Wells et al., *Gene* 34:315–323 (1985); Gilliam et al., *Gene* 12:129–137 (1980); Zoller and Smith, *Methods Enzymol.* 100:468–500 (1983); Dalbadie-McFarland et al., *Proc. Natl. Acad. Sci. (U.S.A.)* 79:6409–6413 (1982); Scharf et al., *Science* 233:1076–1078 (1986); Higuchi et al., *Nucleic Acids Res.* 16:7351–7367 (1988); U.S. Pat. No. 5,811,238, European Patent 0 385 962; European Patent 0 359 472; and PCT Patent Application WO 93/07278; Lanz et al., *J. Biol. Chem.* 266:9971–9976 (1991); Kovgan and Zhdanov, *Biotekhnologiya* 5:148–154, No. 207160n, Chemical Abstracts 110:225 (1989); Ge et al., *Proc. Natl. Acad. Sci. (U.S.A.)* 86:4037–4041 (1989); Zhu et al., *J. Biol. Chem.* 271:18494–18498 (1996); Chu et al., *Biochemistry* 33:6150–6157 (1994); Small et al., *EMBO J.* 11:1291–1296 (1992); Cho et al., *Mol. Biotechnol.* 8:13–16 (1997); Kita et al., *J. Biol. Chem.* 271:26529–26535 (1996); Jin et al., *Mol. Microbiol.* 7:555–562 (1993); Hatfield and Vierstra, *J. Biol. Chem.* 267:14799–14803 (1992); Zhao et al., *Biochemistry* 31:5093–5099 (1992)).

Any of the nucleic acid molecules of the invention may either be modified by site directed mutagenesis or used as, for example, nucleic acid molecules that are used to target other nucleic acid molecules for modification.

It is understood that mutants with more than one altered nucleotide can be constructed using techniques that practitioners are familiar with, such as isolating restriction fragments and ligating such fragments into an expression vector (see, for example, Sambrook et al., *Molecular Cloning: A Laboratory Manual*, Cold Spring Harbor Press (1989)).

Two steps may be employed to characterize DNA-protein interactions. The first is to identify sequence fragments that interact with DNA-binding proteins, to titrate binding activity, to determine the specificity of binding and to determine whether a given DNA-binding activity can interact with related DNA sequences (Sambrook et al., *Molecular Cloning: A Laboratory Manual*, $2^{nd}$ edition, Cold Spring Harbor Laboratory Press, Cold Spring Harbor, N.Y. (1989)). Electrophoretic mobility-shift assay is a widely used assay. The assay provides a rapid and sensitive method for detecting DNA-binding proteins based on the observation that the mobility of a DNA fragment through a nondenaturing, low-ionic strength polyacrylamide gel is retarded upon association with a DNA-binding protein (Fried and Crother, *Nucleic Acids Res.* 9:6505–6525 (1981)). When one or more specific binding activities have been identified, the exact sequence of the DNA bound by the protein may be determined.

Several procedures for characterizing protein/DNA-binding sites are used (Maxam and Gilbert, *Methods Enzymol.* 65:499–560 (1980); Wissman and Hillen, *Methods Enzymol.* 208:365–379 (1991); Galas and Schmitz, *Nucleic Acids Res.* 5:3157–3170 (1978); Sigman et al., *Methods Enzymol.* 208:414–433 (1991); Dixon et al., *Methods Enzymol.* 208:414–433 (1991)). It is understood that one or more of the nucleic acid molecules of the invention may be utilized to identify a protein or fragment thereof that specifically binds to a nucleic acid molecule of the invention. It is also understood that one or more of the protein molecules or fragments thereof of the invention may be utilized to identify a nucleic acid molecule that specifically binds to it.

A two-hybrid system is based on the fact that proteins, such as transcription factors that interact (physically) with one another carry out many cellular functions. Two-hybrid systems have been used to probe the function of new proteins (Chien et al., *Proc. Natl. Acad. Sci. (U.S.A.)* 88:9578–9582 (1991); Durfee et al., *Genes Dev.* 7:555–569 (1993); Choi et al., *Cell* 78:499–512 (1994); Kranz et al., *Genes Dev.* 8:313–327 (1994)).

Interaction mating techniques have facilitated a number of two-hybrid studies of protein-protein interaction. Interaction mating has been used to examine interactions between small sets of tens of proteins (Finley and Brent, *Proc. Natl. Acad. Sci. (U.S.A.)* 91:12098–12984 (1994)), larger sets of hundreds of proteins (Bendixen et al., *Nucl. Acids Res.* 22:1778–1779 (1994)) and to comprehensively map proteins encoded by a small genome (Bartel et al., *Nature Genetics* 12:72–77 (1996)). This technique utilizes proteins fused to the DNA-binding domain and proteins fused to the activation domain. They are expressed in two different haploid yeast strains of opposite mating type and the strains are mated to determine if the two proteins interact. Mating occurs when haploid yeast strains come into contact and result in the fusion of the two haploids into a diploid yeast strain. An interaction can be determined by the activation of a two-hybrid reporter gene in the diploid strain.

It is understood that the protein-protein interactions of protein or fragments thereof of the invention may be investigated using the two-hybrid system and that any of the nucleic acid molecules of the invention that encode such proteins or fragments thereof may be used to transform yeast in the two-hybrid system.

(e) Computer Readable Media

The nucleotide sequence provided in SEQ ID: 1, SEQ ID: 3, SEQ ID: 5, SEQ ID: 7, and SEQ ID: 9 or fragment thereof, or complement thereof, or a nucleotide sequence at least 70% identical, preferably 90% identical even more preferably 99% or about 100% identical to one or more of the nucleic acid sequences provided in SEQ ID: 1, SEQ ID: 3, SEQ ID: 5, SEQ ID: 7, and SEQ ID: 9 or complement thereof or fragments of either, can be "provided" in a variety of mediums to facilitate use.

In a preferred embodiment, 2, preferably 5, more preferably 10, even more preferably 25, 35, 50, or 75 of nucleic acid or amino acid sequences of the present invention can be provided in a variety of mediums.

In another aspect, the nucleotide sequences which correspond to those that encode one or more of the amino acid sequence provided in SEQ ID: 2, SEQ ID: 4, SEQ ID: 6, SEQ ID: 8, and SEQ ID: 10 or fragment thereof can be provided in a variety of mediums to facilitate use.

In another aspect, one or more of the amino acid sequence provided in SEQ ID: 2, SEQ ID: 4, SEQ ID: 6, SEQ ID: 8, and SEQ ID: 10 or fragment thereof, or an amino acid sequence at least 70% identical, preferably 90% identical even more preferably 99% or about 100% identical to the sequence provided in SEQ ID: 2, SEQ ID: 4, SEQ ID: 6, SEQ ID: 8, and SEQ ID: 10 or fragments thereof, can be provided in a variety of mediums to facilitate use.

Such a medium can also provide a subset thereof in a form that allows a skilled artisan to examine the sequences.

In one application of this embodiment, a nucleotide sequence of the invention can be recorded on computer readable media so that a computer-readable medium comprises one or more of the nucleotide sequences of the invention. As used herein, "computer readable media" refers to any medium that can be read and accessed directly by a computer. Such media include, but are not limited to: magnetic storage media, such as floppy discs, hard disc, storage medium and magnetic tape; optical storage media such as CD-ROM; electrical storage media such as RAM and ROM; and hybrids of these categories such as magnetic/optical storage media.

Any number of the sequences, or sequence fragments, of the nucleic acid molecules or proteins of the invention, or fragments of either, can be included, in any number of combinations, on a computer-readable medium.

By providing one or more of nucleotide sequences of the invention, a skilled artisan can routinely access the sequence information for a variety of purposes. Computer software is publicly available that allows a skilled artisan to access sequence information provided in a computer readable medium. The examples which follow demonstrate how software which implements the BLAST (Altschul et al., *J.* *Mol. Biol.* 215:403–410 (1990)) and BLAZE (Brutlag et al., *Comp. Chem.* 17:203–207 (1993)) search algorithms on a Sybase system can be used to identify open reading frames (ORFs) within the genome that contain homology to ORFs or proteins from other organisms.

The invention further provides systems, particularly computer-based systems, which contain the sequence information described herein. Such systems are designed to identify commercially important fragments of the nucleic acid molecule of the invention. As used herein, "a computer-based system" refers to the hardware means, software means and data storage means used to analyze the nucleotide sequence information of the invention. The minimum hardware means of the computer-based systems of the invention comprises a central processing unit (CPU), input means, output means and data storage means. A skilled artisan can readily appreciate that any one of the currently available computer-based system are suitable for use in the invention.

A variety of comparing means can be used to compare a target sequence or target motif with the data storage means to identify sequence fragments sequence of the invention. For example, implementing software which implement the BLAST and BLAZE algorithms (Altschul et al., *J. Mol. Biol.* 215:403–410 (1990)) can be used to identify open frames within the nucleic acid molecules of the invention. A skilled artisan can readily recognize that any one of the publicly available homology search programs can be used as the search means for the computer-based systems of the invention.

Having now described the invention, the following examples are provided by way of illustration and are not intended to limit the scope of the invention, unless specified.

EXAMPLE 1

Nucleic acid sequences encoding proteins are identified from the NCBI nr.aa database searched with BLASTX (default values) using full length insert sequences as queries (see Table 1) with a cutoff parameter of 1e-8.

| Seq Num | Seq ID | Library | NCBI gi number | BLAST score | E value | % Ident | Qstart–Qend (nt) | Sstart–Send (aa) | coding seq | pep num | Complete or partial | NCBI gi description |
|---|---|---|---|---|---|---|---|---|---|---|---|---|
| 1 | fCzmst_1700335924 | SATMONO19 | 3044214 | 1087 | 0.0 | 78 | 118–2100 | 4–664 | 1–2103 | 2 | Partial | gi\|3044214\| gb\|AAC13498.1\| (AF057044) acyl-CoA oxidase [*Arabidopsis thaliana*] |
| 3 | fC-zmst_1700336272 | SATMONO19 | 1066163 | 538 | 1e-152 | 79 | 13–1011 | 129–461 | 1–1017 | 4 | Partial | gi\|1066163\| emb\|CAA63598.1\| (X93015) glyoxysomal beta-ketoacyl-thiolase [*Brassica napus*] |
| 5 | GLYma; Acx1; 2 | Clontech cat# FL1062a (10 day soy seedlings) | 3044213 | 1109 | 0.0 | 80 | 119–2113 | 1–664 | 119–2116 | 6 | Complete | AF057044 *Arabidopsis thaliana* acyl-CoA oxidase (ACX1) mRNA |
| 7 | GLYma, thiolase | N/A | 1694621 | 716 | 0.0 | 77 | 48–1430 | 1–461 | 48–1439 | 8 | Complete | 3-ketoacyl-CoA thiolase (Cucurbita sp.) |
| 9 | GLYma; Acx1; 1 | Clontech cat# FL1062a (10 day soy seedlings) | 3044213 | 1083 | 0.0 | 79 | 146–2131 | 2–664 | 140–2134 | 10 | Complete | AF057044 *Arabidopsis thaliana* acyl-CoA oxidase (ACX1) mRNA |

The entries in the Seq Num column refer to the corresponding sequence in the sequence listing.

Seq ID

The Seq ID is the name of the insert sequence in a particular clone found in the PhytoSeq or SEQDB databases. The clone ID is found after the "_" character. If there is no "_" character, the Seq ID is the same as the clone ID. Each Seq ID entry in the table refers to the clone whose sequence is used for the sequence comparison whose scores are presented.

Library

The entries in the "Library" column refer to the cDNA library from which the clone is obtained. The libraries are as follows: the SATMON019 cDNA library is generated from *Zea mays* L. (DK604, Dekalb Genetics, Dekalb, Ill. U.S.A.) culm (stem) at the V8 developmental stage. The Clonetech cat#FL1062a cDNA library is from 10 day old soy seedlings. In the case where N/A is listed under library, RT-PCR is done using degenerate oligos corresponding to regions which are highly conserved among known plant thiolase sequences. The template used for PCR is first strand cDNA made from cotyledon tissue from 2 day old soybean seedlings. The PCR fragment that is obtained from the above reaction is sequenced and has homology to thiolases. If the fragment does not cover the full-length of the cDNA, primers are designed for 5' and 3' RACE. Based on the sequence of the PCR fragments that are obtained from a) RT-PCR, b) 5' RACE PCR and c) 3' RACE PCR, two primers are designed which span the entire cDNA. To eliminate errors due to PCR or sequencing, multiple independent PCR reactions are done, followed by multiple ligations, followed by sequencing of multiple clones per ligation. Also, high fidelity Taq polymerases are used to eliminate PCR errors. The full-length sequence is compiled from the sequencing reactions that are obtained from multiple clones.

NCBI gi Number

Each sequence in the GenBank public database is arbitrarily assigned a unique NCBI gi (National Center for Biotechnology Information GenBank Identifier) number. In this table, the NCBI gi number which is associated (in the same row) with a given clone refers to the particular GenBank sequence which is used in the sequence comparison.

Blast Bit Score

Bit score for BLAST match score that is generated by sequence comparison of the full length with the GenBank sequence listed in the Description column.

E-Value

The entries in the E-Value column refer to the probability that such matches occur by chance.

%Ident

The entries in the "%Ident" column of the table refer to the percentage of identically matched nucleotides (or residues) that exist along the length of that portion of the sequences which is aligned by the BLAST comparison to generate the statistical scores presented.

Qstart-Qend

The entries in the "QStart" column refer to the location of the nucleotide in the designated clone that first matches with the designated NCBI sequence QEnd" column refer to the location of the nucleotide in the designated clone that ends the match with the designated NCBI sequence.

SStart

The entries in the "SStart" column refer to the location of the amino acid in the designated NCBI sequence that is first matched with a sequence in the designated clone. SEnd" refers to the location of the amino acid in the designated NCBI sequence.

Coding Seq

The entries in this column refer to the nucleotide where translation begins and ends pep num The entries in this column refer to the number of the translated nucleotide sequence in the sequence listing Complete or Partial The entries in this column describe the relative placement of the longest ORF and the BLAST results. A sequence is listed as "partial" if the query sequence contains a complete open reading frame 1) with the starting codon (ATG) located greater than 30 bp from the 5' end and the subject sequence does not contain an ATG 2) the query sequence contains no ATG or start codon or 3) the query sequence ATG position is greater than 30 bp from the 5' end and there is no matching subject sequence. A sequence is referred to as "complete" if the query sequence contains a complete open reading frame and 1) the query sequence ATG position is less than 30 bases from the 5'end and there is no matching subject sequence 2) the query sequence ATG is greater than 30 bp from the 5' end and the subject sequence does not have an ATG NCBI gi Description The "NCBI gi Description" column provides a description of the NCBI gi referenced in the "NCBI gi" column.

EXAMPLE 2

SEQ ID: 1, SEQ ID: 3, SEQ ID: 5, SEQ ID: 7, and SEQ ID: 9 correspond to the sequence of the entire cDNA inserts of the clones set forth in Table 1. The deduced amino acid sequence for these DNA sequences (SEQ ID: 2, SEQ ID: 4, SEQ ID: 6, SEQ ID: 8, and SEQ ID: 10) is determined using the Translation program in LifeTools™ (Incyte Pharmaceuticals Inc., Palo Alto, Calif.), Finishing Manager (Millenium Pharmaceuticals, Cambridge, Mass.) or similar translation program.

REFERENCES

All references cited above are incorporated by reference in their entirety. In addition, these references can be relied upon to make and use aspects of the invention.

We claim:

1. A substantially purified nucleic acid molecule comprising the nucleic acid sequence of SEQ ID NO: 1 or its complement.

2. A cell or plant comprising a heterologous nucleic acid molecule comprising a nucleic acid sequence of SEQ ID NO: 1 or its complement.

3. The cell or plant according to claim 2, wherein said cell or plant is a plant cell or plant.

4. The cell or plant according to claim 3, wherein said cell or plant is a plant cell or plant.

* * * * *

UNITED STATES PATENT AND TRADEMARK OFFICE
CERTIFICATE OF CORRECTION

PATENT NO.    : 6,518,488 B1       Page 1 of 1
DATED         : February 11, 2003
INVENTOR(S)   : Agarwal et al.

It is certified that error appears in the above-identified patent and that said Letters Patent is hereby corrected as shown below:

<u>Column 1,</u>
Line 5, please insert the following:
      -- INCORPORATION OF SEQUENCE LISTING
    A paper copy of the Sequence Listing and a computer readable form of the sequence listing on diskette, containing the file named SeqList.txt, which is 115,066 bytes in size (measured in MS-DOS), and which was created on April 11, 2002, are herein incorporated by reference. --

Signed and Sealed this

Twenty-seventh Day of May, 2003

JAMES E. ROGAN
*Director of the United States Patent and Trademark Office*